US012728221B2

(12) United States Patent
Qureshi et al.

(10) Patent No.: US 12,728,221 B2
(45) Date of Patent: Sep. 8, 2026

(54) APPARATUSES AND METHODS TO ACTIVATE MUSCLES OF DEGLUTITION TO PROMOTE DYSPHAGIA RECOVERY IN NEUROLOGICAL DISORDERS

(71) Applicant: DyQure LLC, Sauk Rapids, MN (US)

(72) Inventors: Adnan I. Qureshi, Columbia, MO (US); Muhammad Fareed Khan Suri, Sauk Rapids, MN (US)

(73) Assignee: DyQure LLC, Sauk Rapids, MN (US)

(*) Notice: Subject to any disclaimer, the term of this patent is extended or adjusted under 35 U.S.C. 154(b) by 996 days.

(21) Appl. No.: 17/901,303

(22) Filed: Sep. 1, 2022

(65) Prior Publication Data

US 2024/0075229 A1 Mar. 7, 2024

(51) Int. Cl.

| | |
|---|---|
| ***A61M 25/00*** | (2006.01) |
| ***A61M 16/04*** | (2006.01) |
| ***A61M 25/10*** | (2013.01) |

(52) U.S. Cl.

CPC .... *A61M 16/0477* (2014.02); *A61M 25/0026* (2013.01); *A61M 25/10184* (2013.11)

(58) Field of Classification Search

CPC ................ A61H 9/0071; A61H 21/00; A61M 25/10184; A61N 2005/0609; A61N 2005/0662; A61N 2005/063

See application file for complete search history.

(56) References Cited

U.S. PATENT DOCUMENTS

2006/0095032 A1* 5/2006 Jackson .......... A61M 25/10184 606/41

FOREIGN PATENT DOCUMENTS

| | | | | |
|---|---|---|---|---|
| CN | 213609296 U * | 7/2021 | | |
| JP | 2015016137 A | 1/2015 | | |
| KR | 1020130055675 A | 5/2013 | | |
| KR | 1020160112418 A | 9/2016 | | |
| WO | WO-2012134196 A2 * | 10/2012 | .......... | A61J 15/0049 |

OTHER PUBLICATIONS

Korean Intellectual Property Office, Written Opinion of the International Searching Authority and International Search Report with Notice, PCT/US2023/031891, 14 pages.

(Continued)

*Primary Examiner* — Deanna K Hall

(74) *Attorney, Agent, or Firm* — Bradley J. Thorson; DeWitt LLP

(57) ABSTRACT

Apparatuses and methods for treating dysphagia related to neurological disease, and promoting deglutition. The apparatus includes a tube with inner diameter larger than the outer diameter of a standard nasogastric/enteric tube, and can be advanced over the standard nasogastric/enteric tube platform through the oropharynx and esophagus into the stomach. The apparatus sequentially stimulates muscles involved in deglutition (swallowing) to monitor and promote recovery from dysphagia. Another iteration uses a long sleeve placed circumferentially around the standard nasogastric/enteric tube. The sleeve can be inflated in the proximal portion using a bolus of air or another solution and the bolus can move down the sleeve propelled by contraction of oropharyngeal and esophageal muscles with segmentation ensured by valves or adhesions at regular intervals.

22 Claims, 22 Drawing Sheets

(56) References Cited

OTHER PUBLICATIONS

Cohen, D.G., Roffe, C., Beavan, J et al., Post-stroke dysphagia: A review and design consideration for future trials, International Journal of Stroke. 2016;11(4):399-411.
Speyer, R., Baijens, L., Heijnen, M., Zwijnenberg, I., Effects of Therapy in Oropharyngeal Dysphagia by Speech and Language Therapists: A Systematic Review, Dysphagia 2010; 25: 40-65, Published online Sep. 17, 2009.
Geeganage, C., Beavan, J., Bath, P.M.W., Interventions for dysphagia and nutritional support in acute and subacute stroke (Review), Cochrane Database Syst Rev 2012; 10: CD000323.
Bulow, M., Speyer, Renee, Baijens, L., Woisard, V., Ekberg, O., Neuromuscular Electrical Stimulation (NMES) in Stroke Patients with Oral and Pharyngeal Dysfunction, Dysphagia, 2008;23(3):302-309, Published online Apr. 25, 2008.
Ludlow, C., Humbert, I., Saxon, K., Poletto, C., Sonies, B., Crujido, L.., Effects of Surface Electrical Stimulation Both at Rest and During Swallowing in Chronic Pharyngeal Dysphagia, Dysphagia. Jan. 2007; 22(1):1-10.

* cited by examiner

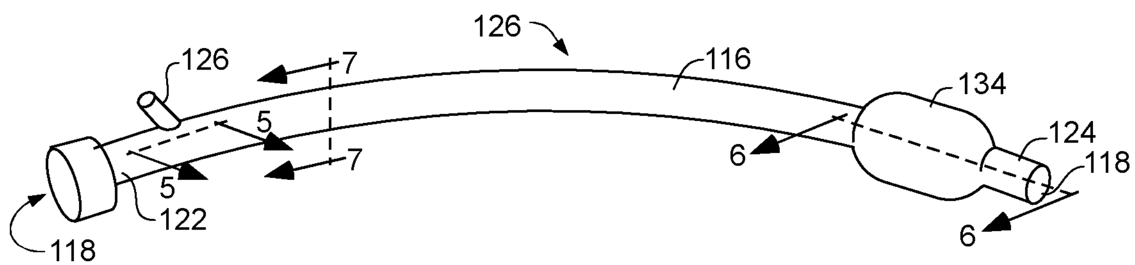
FIG. 4
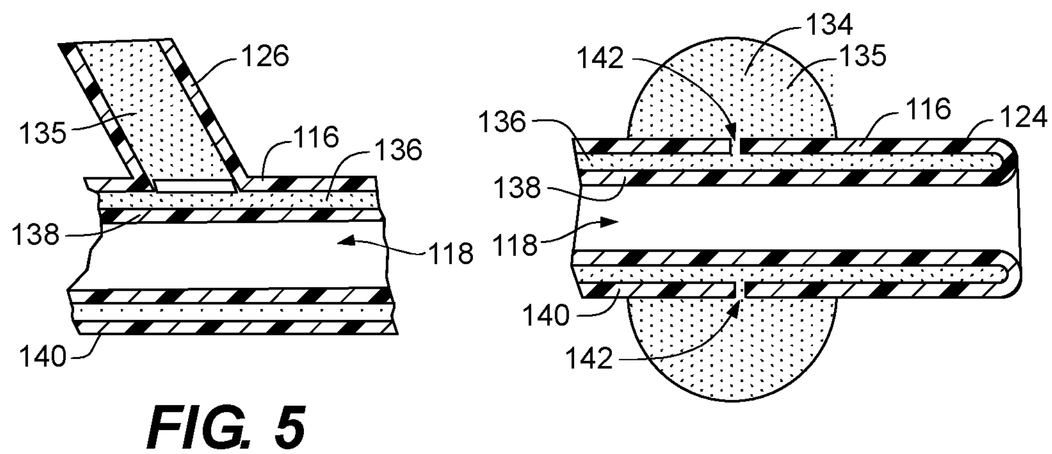
FIG. 5
FIG. 6
126
116
138
118
140
136
FIG. 7

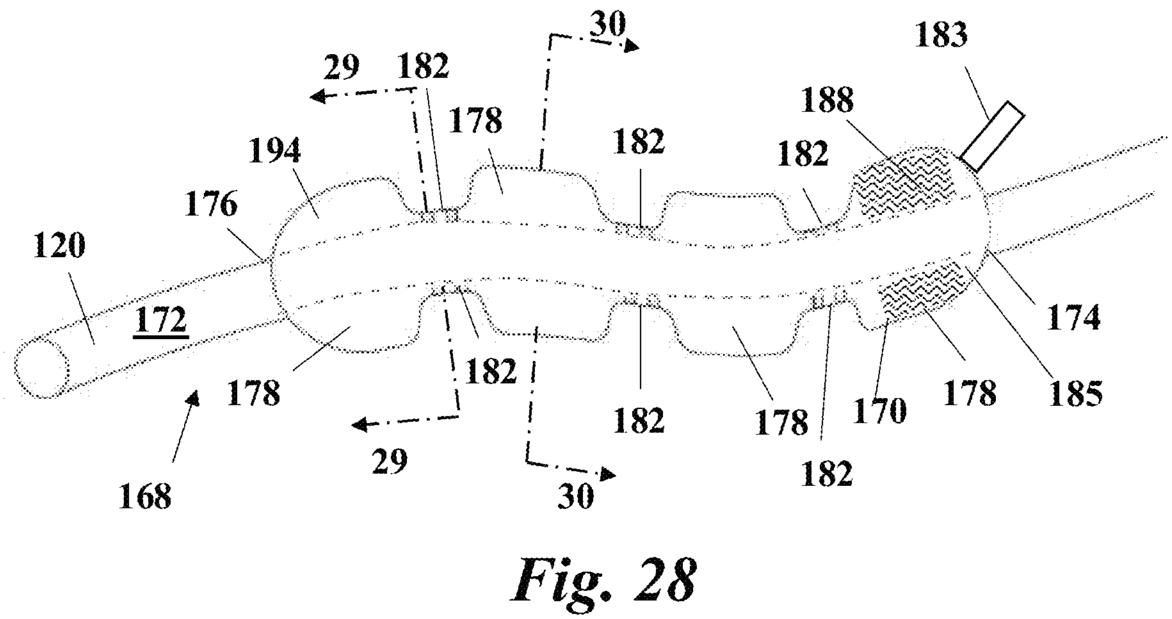
Fig. 28
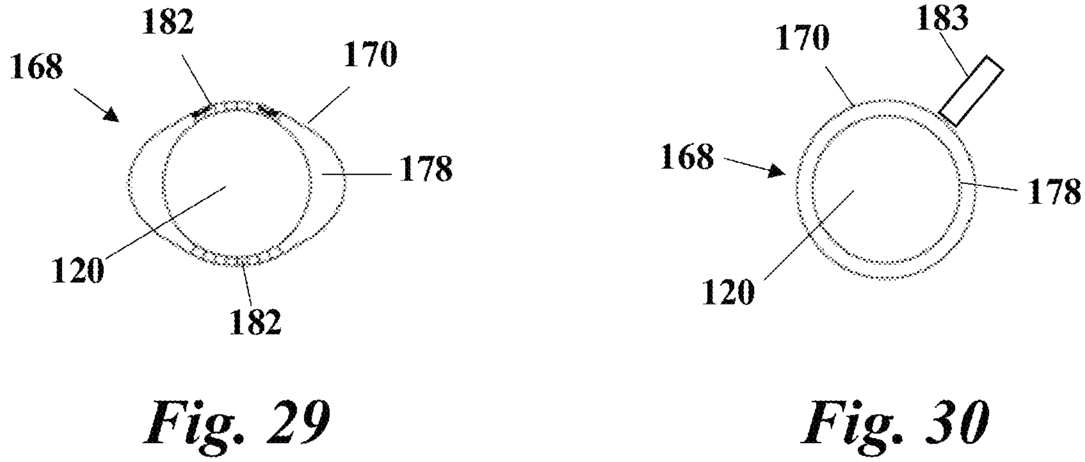
Fig. 29
Fig. 30

APPARATUSES AND METHODS TO ACTIVATE MUSCLES OF DEGLUTITION TO PROMOTE DYSPHAGIA RECOVERY IN NEUROLOGICAL DISORDERS

TECHNICAL FIELD

The invention addresses apparatuses and treatments for promoting recovery of deglutition (swallowing) in patients with dysphagia secondary to neurological disorders.

BACKGROUND

Dysphagia affects more than 50% of stroke survivors and is associated with two-fold higher risk of pneumonias and deaths (Cohen D L, Roffe C, Beavan J, et al. *International Journal of Stroke.* 2016; 11(4):399-411; Speyer, R, Baijens, L, Heijen, M, Zwijnenberg, I. Dysphagia 2010; 25: 40-65). No effective treatment for dysphagia has been available before (Geeganage, C, Beavan, J, Ellender, S, Bath, P M. Cochrane Database Syst Rev 2012; 10: CD000323). Dysphagia associated with neurological diseases is unique because there is no mechanical obstruction and muscles involved are structurally intact. Rehabilitation techniques such as oral and lingual exercises tend to focus on strength and endurance but require voluntary effort and are unable to mimic the dynamic process of deglutition. Neuromuscular stimulation of the oropharynx using surface stimulation has demonstrated some improvement in dysphagia but most stimulations are too weak or do not penetrate deep enough to stimulate the muscles responsible for deglutition. (Bulow M, Speyer R, Baijens L, Woisard V, Ekberg O. *Dysphagia.* 2008; 23(3):302-309; Ludlow C L, Humbert I, Saxon K, Poletto C, Sonies B, Crujido L. *Dysphagia.* 2006 doi: 10.1007/s00455-006-9029-4). The proposed methodologies and apparatuses allow reproducing the dynamic nature of deglutition and involves activation of both oropharyngeal and esophageal components.

What is needed are apparatuses and methods for effectively treating dysphagia in patients with neurological disease.

SUMMARY

Embodiments of the invention address the need for apparatuses and methods for effectively treating dysphagia in patients with neurological disease. Patients with neurological disease who have dysphagia will undergo placement of a nasogastric/enteric tube for purposes of nutrition, hydration, and medication intake. The dysphagia treatment apparatus described herein can be used concurrently with a standard nasogastric/enteric tube to ensure that any additional insertion of new devices in the oropharynx is not necessary. The dysphagia treatment apparatus is emplaced through the oropharynx and esophagus over a standard nasogastric tube already positioned, and position can be confirmed using a combination of bed side test and radiography. The dysphagia treatment apparatus is focused on providing mechanical, and in another embodiment, light stimulation of muscles involved in deglutition to sequentially stimulate these muscles promoting recovery in strength and coordination. Advancement of the device with various iterations for mechanical or light stimulation multiple times a day with or without concurrent electrical stimulation is synonymous with active and passive activation of other paralyzed muscles in patients with neurological diseases that forms the basis of rehabilitation. The activation can be performed at bedside without complicated equipment or imaging techniques.

In an embodiment, an apparatus for treating dysphagia includes an elongate tubular body presenting a proximal end, a distal end, and defining a first lumen and a second lumen. The first lumen is oriented along a longitudinal axis of the tubular body and adapted to receive a nasogastric/enteric tube therein such that the elongate tubular body is selectively slidably shiftable relative to the nasogastric/enteric tube, the second lumen being oriented parallel to the first lumen. A dysphagia treatment device is disposed proximate the distal end of the elongate tubular body, and the dysphagia treatment device is selectively actuatable as the elongate tubular body slides over the nasogastric/enteric tube.

In an embodiment, the dysphagia treatment device is an inflatable balloon, the balloon being selectively inflatable with fluid supplied through the second lumen. At least one pressure transducer for measuring fluid pressure in the balloon can be provided and the at least one pressure transducer can be communicatively coupled to an external display. The tubular body can include a port disposed proximate the proximal end of the tubular body and fluidly coupled to the second lumen for supplying and removing fluid from the second lumen and the balloon. The second lumen can be concentric with the first lumen.

In an embodiment, the dysphagia treatment device can include at least one air nozzle extending from the second lumen to an exterior surface of the tubular body, the at least one air nozzle oriented transverse to the longitudinal axis of the tubular body. At least one pressure transducer can be disposed at the distal end of the elongate tubular body and communicatively coupled to an external display. A port can be disposed proximate the proximal end of the tubular body and fluidly coupled to the second lumen for supplying air to the second lumen and the at least one air nozzle. The second lumen can be concentric with the first lumen.

In an embodiment, the dysphagia treatment device includes at least one light emitter arranged to emit light in a direction transverse to the longitudinal axis of the tubular body. The at least one light emitter can emit light pulses having a wavelength in a range of from about 400 nm to about 600 nm and a duration in a range of from about 10 ms to about 100 ms. The at least one light emitter can be an LED. The apparatus can include at least one pressure transducer disposed at the distal end of the elongate tubular body, and the at least one pressure transducer can be communicatively coupled to an external display. A high-resolution camera can be disposed at the distal end of the tubular body, the camera communicatively coupled to a video display. The second lumen can be concentric with the first lumen.

In an embodiment, an apparatus for treating dysphagia includes a nasogastric/enteric tube and a sleeve disposed on an exterior surface of the nasogastric/enteric tube. The sleeve is formed from a resilient, flexible polymer material and divided into a plurality of inflatable chambers with a plurality of dividers, each one of the plurality of chambers partially separated from an adjacent one of the plurality of chambers by a separate one of the dividers, a proximal end of the sleeve being fluidly coupled to an injection port for injecting fluid into the sleeve. Each of the plurality of dividers can be a non-compliant ring of polymer material. In another embodiment, each of the plurality of dividers can be a portion of the sleeve adhered to the exterior surface of the nasogastric/enteric tube. In another embodiment, each of the plurality of dividers can be a flexible septum extending from an interior surface of the sleeve toward the exterior surface of the nasogastric/enteric tube. At least one pressure transducer can be disposed on the sleeve or the nasogastric/enteric tube. And the at least one pressure transducer can be communicatively coupled to an external display. An aspiration port can be fluidly coupled to a distal end of the sleeve.

In another embodiment, a method for treating dysphagia includes providing a dysphagia treatment apparatus including an elongate tubular body presenting a proximal end, a distal end, and defining a first lumen and a second lumen. The first lumen is oriented along a longitudinal axis of the tubular body, and adapted to receive a nasogastric/enteric tube therein such that the elongate tubular body is selectively slidably shiftable relative to the nasogastric/enteric tube. The second lumen is oriented parallel to the first lumen, and a dysphagia treatment device is disposed proximate the distal end of the elongate tubular body. A proximal end of a nasogastric/enteric tube emplaced in the nasopharynx and esophagus of a patient is introduced into the first lumen at the distal end of the elongate tubular body. The elongate tubular body is slid over the nasogastric/enteric tube to advance the elongate tubular body into the nasopharynx and esophagus of the patient while periodically actuating the dysphagia treatment device to stimulate muscles controlling deglutition in the nasopharynx and esophagus of the patient.

In an embodiment, the dysphagia treatment device can include an inflatable balloon, and the step of actuating the dysphagia treatment device can include inflating the balloon with fluid.

In another embodiment, the dysphagia treatment device includes at least one air nozzle, and the step of actuating the dysphagia treatment device includes applying pulses of air to the nasopharynx and esophagus of the patient with the at least one air nozzle. The air pulses can have a pressure in a range of about 70 mm Hg to about 110 mm Hg.

In another embodiment, the dysphagia treatment device can include at least one light emitter, and the step of actuating the dysphagia treatment device can include applying pulses of light to the nasopharynx and esophagus of the patient with the at least one light emitter. The light pulses can have a wavelength in a range of from about 400 nm to about 600 nm and a duration in a range of from about 10 ms to about 100 ms.

In another embodiment, a method for treating dysphagia includes providing a dysphagia treatment apparatus including a nasogastric/enteric tube and a sleeve disposed on an exterior surface of the nasogastric/enteric tube. The sleeve is formed from a resilient, flexible polymer material and divided into a plurality of inflatable chambers with a plurality of dividers, each one of the plurality of chambers partially separated from an adjacent one of the plurality of chambers by a separate one of the dividers. A proximal end of the sleeve is fluidly coupled to an injection port for injecting fluid into the sleeve. The nasogastric/enteric tube with sleeve is emplaced into the nasopharynx and esophagus of a patient and a fluid is injected into a proximal-most one of the plurality of chambers to inflate the chamber.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The subject matter hereof may be more completely understood in consideration of the following detailed description of various embodiments in connection with the accompanying figures, in which:

FIG. 4 is an isometric view of an apparatus for treating dysphagia according to an embodiment of the invention, in which the apparatus includes a selectively inflatable balloon proximate a distal end of the apparatus;

FIG. 5 is a cross-sectional view of the apparatus of FIG. 4, taken at section 5-5 of FIG. 4;

FIG. 6 is a cross-sectional view of the apparatus of FIG. 4, taken at section 6-6 of FIG. 4;

FIG. 7 is a cross-sectional view of the apparatus of FIG. 4, taken at section 7-7 of FIG. 4;

FIG. 28 is an isometric view of a sleeve receivable over a standard nasogastric tube including adhesions to secure the outer portion of the sleeve to a central lumen of the device;

FIG. 29 is a cross-sectional view taken at section 29-29 of FIG. 28;

FIG. 30 is a cross-sectional view taken at section 30-30 of FIG. 28;

Figure 1:
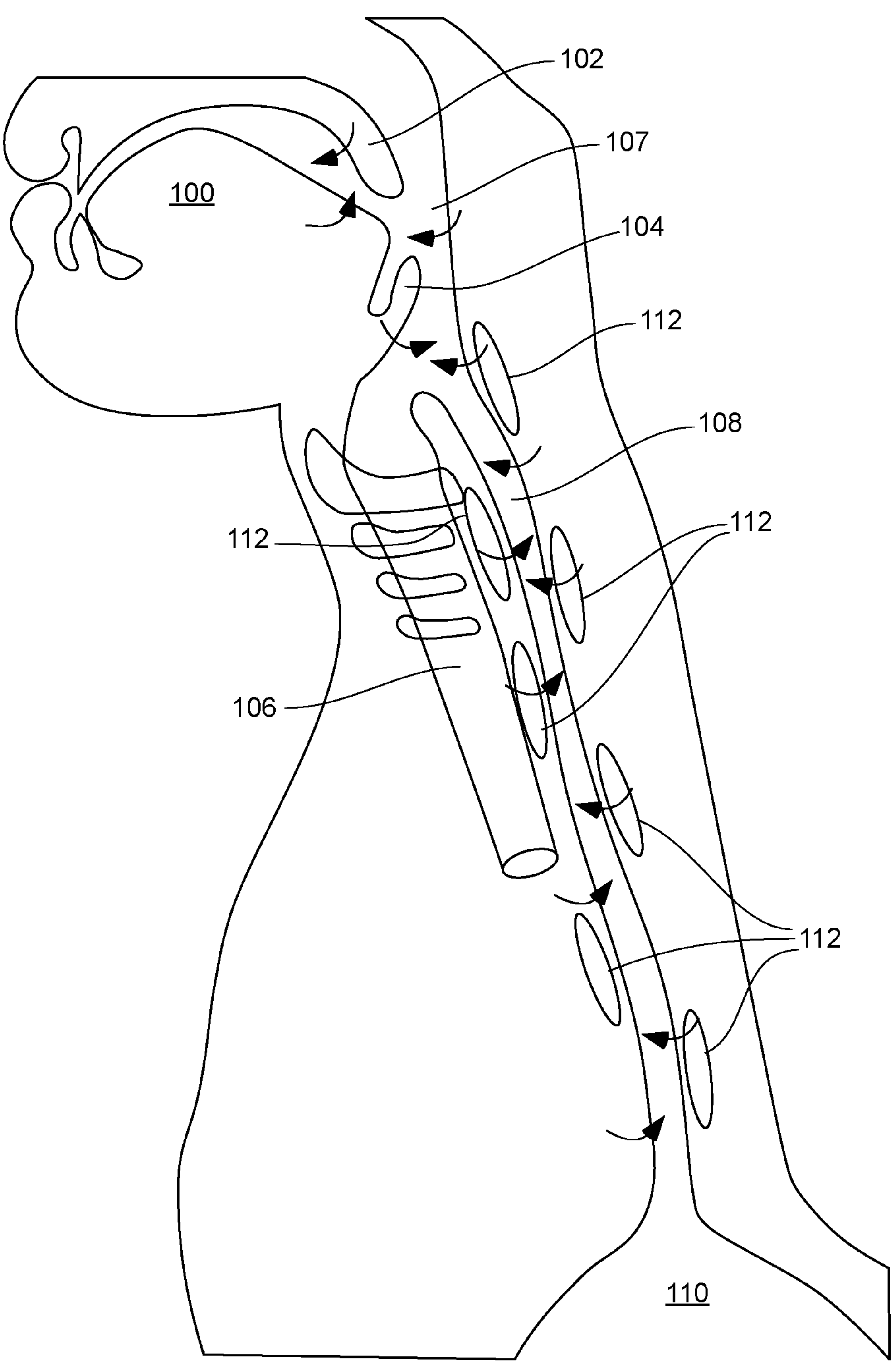
FIG. 1 depicts the anatomy of the oropharynx and esophagus, with the muscle contractions facilitating deglutition.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

In FIG. 1, there is depicted a cross-section of human anatomy, including tongue 100, palate 102, epiglottis 104, trachea 106, oropharynx 107, esophagus 108, stomach 110, and muscles 112. During the process of deglutition, muscles 112 sequentially contract as depicted by the arrows, enabling food and water to be moved from oropharynx 107 through esophagus 108 to stomach 110.

Figure 2:
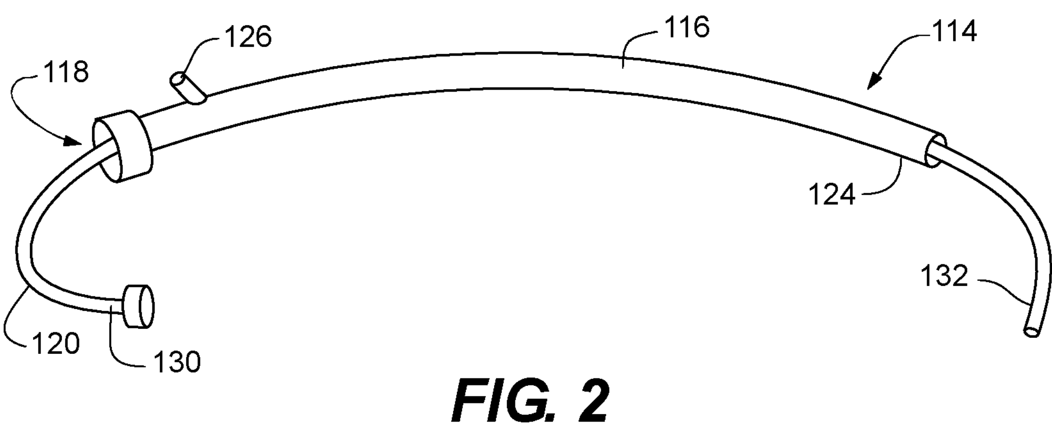
FIG. 2 is an isometric view of an apparatus for treating dysphagia according to an embodiment of the invention.
Figure 3:
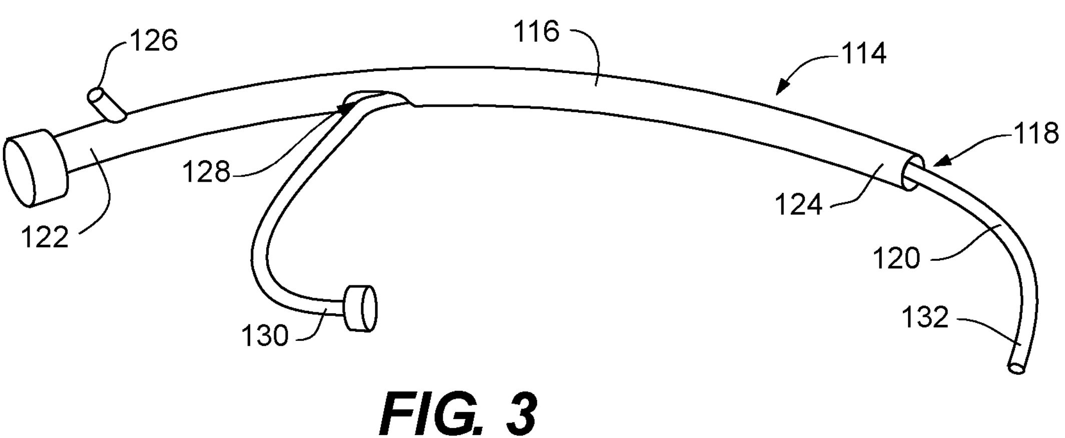
FIG. 3 is an isometric view of an apparatus for treating dysphagia according to another embodiment of the invention.

FIG. 2 depicts a dysphagia treatment apparatus 114 according to an embodiment of the invention. Apparatus 114 generally includes tubular body 116, which defines lumen 118. Lumen 118 has an inner diameter sized to receive a standard nasogastric/enteric tube 120 having a diameter of 12 to 18 French (4 to 6 mm) therethrough, so that apparatus 114 is slidable on nasogastric/enteric tube 120. Lumen 118 extends from proximal end 122 to distal end 124. In a non-limiting embodiment, tubular body 116 can have a length of 42 to 50 inches and markings at 18, 22, 26 and 30 inches (not depicted) to help ensure proper insertion and placement in the oropharynx and esophagus. Port 126 is provided to enable injection of air, or liquid such as saline, into a second lumen (not depicted), as will be further described hereinbelow. In the alternative embodiment of FIG. 3, tubular body 116 defines aperture 128 connected to lumen 118 enabling nasogastric tube 120 to extend therethrough rather than through proximal end 122.

In use, the apparatus of FIG. 2 can be advanced into oropharynx 107 and esophagus 108 by introducing proximal end 130 of nasogastric/enteric tube 120, which is already in place in oropharynx 107 and esophagus 108, into lumen 118 at distal end 124. Dysphagia treatment apparatus 114 can then be slid over nasogastric/enteric tube 120 until proximal end 130 of nasogastric/enteric tube 120 protrudes from proximal end 122 and distal end 132 of nasogastric/enteric tube 120 protrudes from distal end 124 as depicted. In the alternative embodiment of FIG. 3, proximal end 130 of nasogastric/enteric tube 120 is introduced into lumen 118 at distal end 124, but proximal end 130 of nasogastric/enteric tube 120 exits through aperture 128 as dysphagia treatment apparatus 114 is slid over nasogastric/enteric tube 120. In both embodiments, proximal end 122 of dysphagia treatment apparatus 114 and proximal end 130 of nasogastric/enteric tube 120 remain outside oropharynx 107.

In the embodiment depicted in FIGS. 4-11, dysphagia treatment apparatus 114 has inflatable balloon 134 disposed proximate distal end 124. Balloon 134 can be coated with sugar to mimic the taste of food. Second lumen 136 is defined between inner wall 138 and outer wall 140 of tubular body 116. Second lumen 136 is fluidly coupled to inflatable balloon 134 through ports 142, and to port 126. It will be appreciated that, although second lumen 136 is depicted as being concentric with lumen 118, second lumen 136 could be non-centrically disposed and run parallel to lumen 118 in other embodiments.

Figure 8:
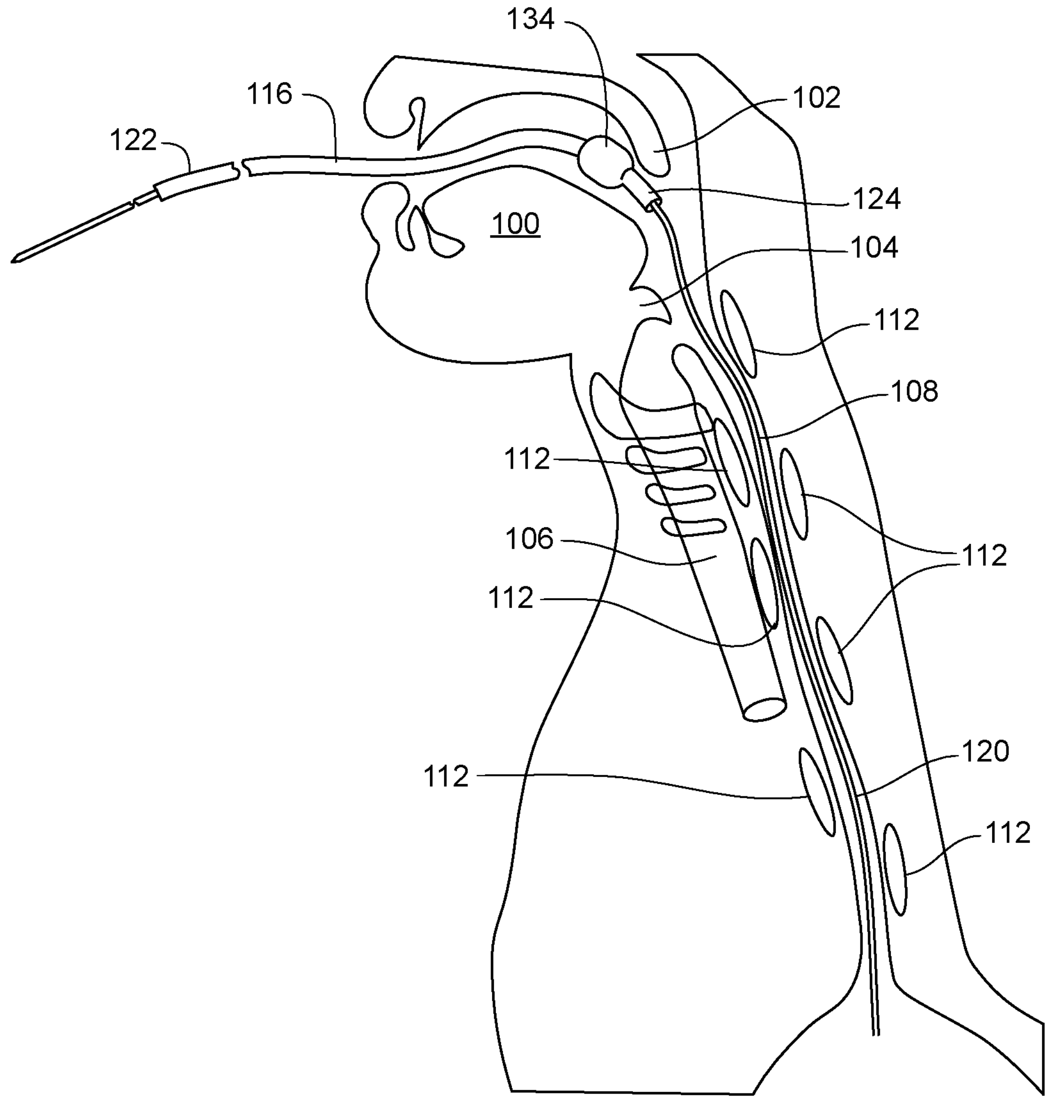
FIG. 8 depicts the apparatus of FIG. 4 in a first stage of advancement into the oropharynx and esophagus over a standard nasogastric tube.
Figure 9:
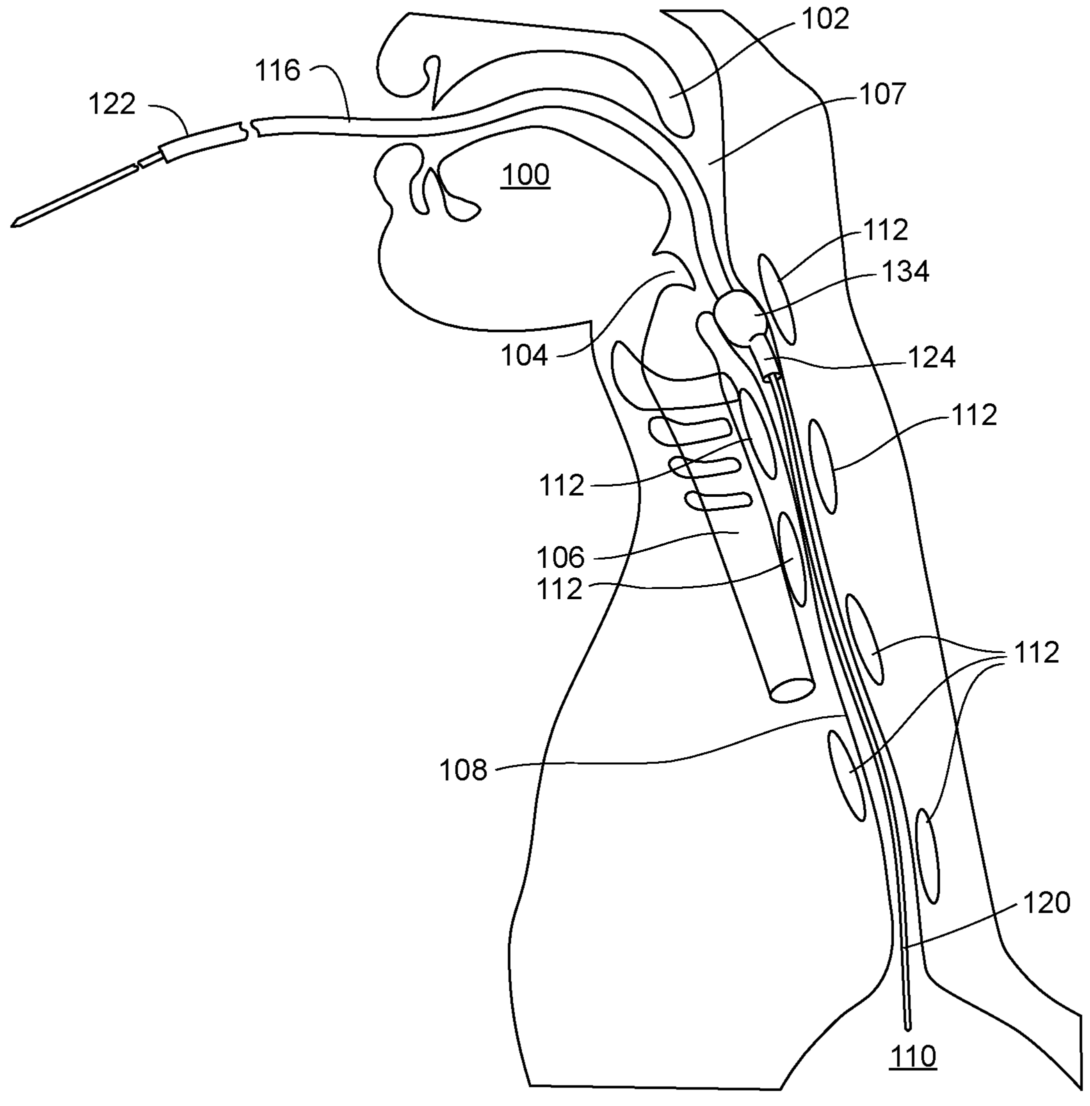
FIG. 9 depicts the apparatus of FIG. 4 in a second stage of advancement into the oropharynx and esophagus over a standard nasogastric tube.
Figure 10:
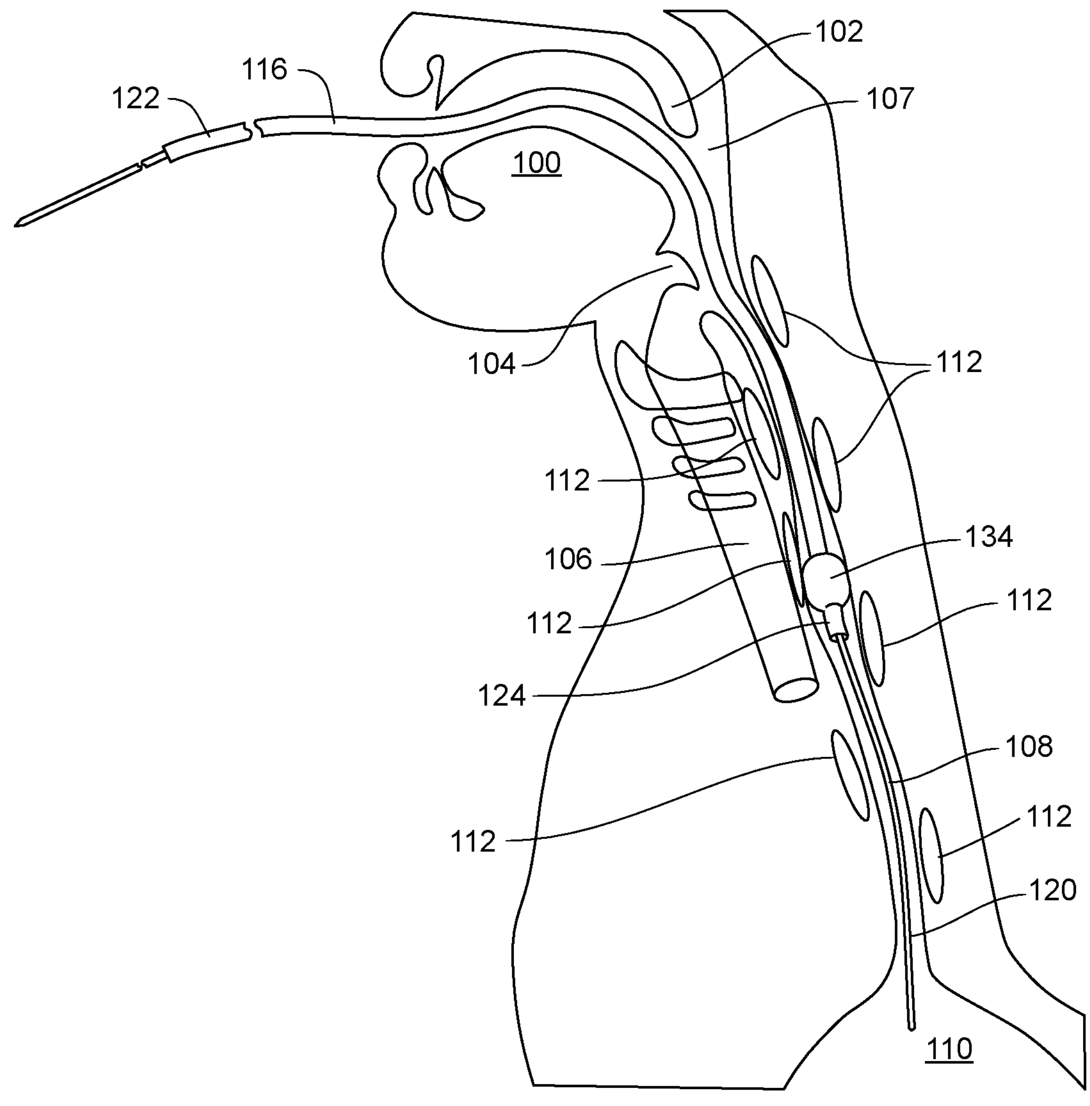
FIG. 10 depicts the apparatus of FIG. 4 in a third stage of advancement into the oropharynx and esophagus over a standard nasogastric tube.
Figure 11:
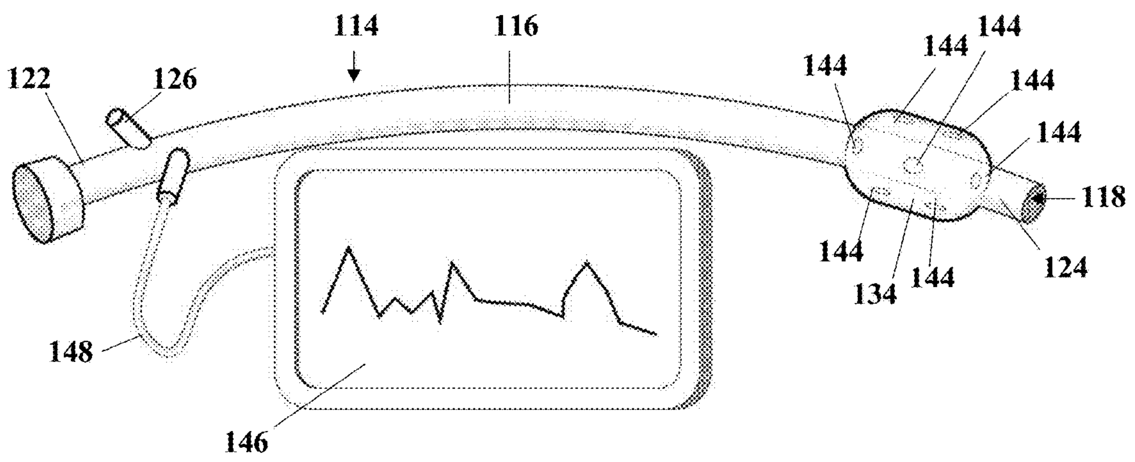
FIG. 11 is an isometric view of the apparatus of FIG. 4, including a display for displaying pressure within the inflatable balloon.
Figure 12:
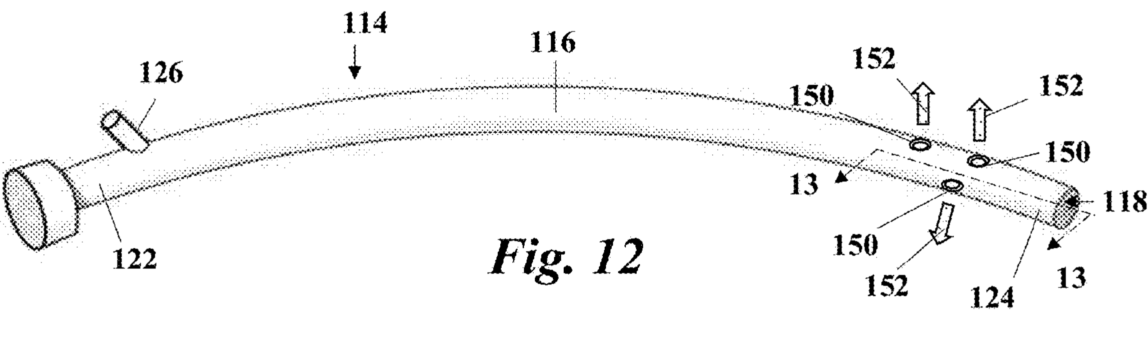
FIG. 12 is an isometric view of an apparatus for treating dysphagia according to another embodiment of the invention, in which the apparatus includes ports proximate a distal end of the apparatus for applying air puffs to the oropharynx and esophagus.
Figure 13:
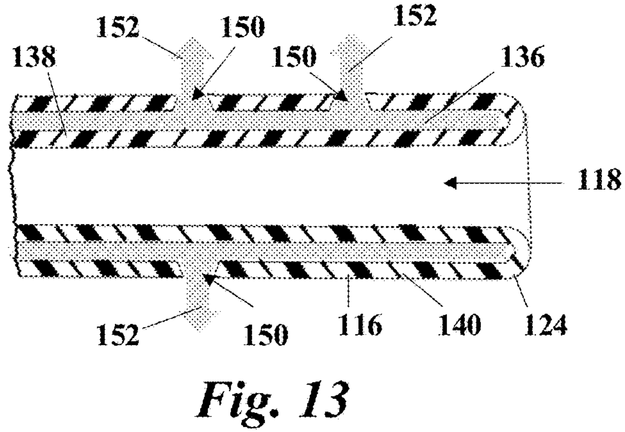
FIG. 13 is a cross-sectional view of the apparatus of FIG. 12, taken at section 13-13 of FIG. 12.

In use as depicted in FIGS. 8-10, dysphagia treatment apparatus 114 is advanced into oropharynx 107 and esophagus 108 by introducing proximal end 130 of nasogastric/enteric tube 120 into lumen 118 at distal end 124. As depicted in FIG. 8, once balloon 134 is inside oropharynx 107, balloon 134 is inflated with a fluid such as pressurized air supplied through port 126, and into second lumen 136 and balloon 134 through ports 142. It will be appreciated that other fluids such as saline or other liquid could be substituted for pressurized air. As depicted in FIG. 11, one or more pressure transducers 144 can be disposed inside balloon 134 and communicatively coupled with external display 146 to enable monitoring and recording of air pressure inside balloon 134 as dysphagia treatment apparatus 114 is advanced further into oropharynx 107 and esophagus 108 along nasogastric/enteric tube 120. This enables measurement and tracking of changes in pressure due to contraction of muscles 112 in oropharynx 107 and esophagus 108 as part of deglutition in response to forward movement of balloon. It will be appreciated that, although external display 146 is depicted as being coupled to pressure transducers 144 through wire 148, external display 146 could also be coupled through a wireless connection.

As dysphagia treatment apparatus 114 is advanced further into esophagus 108 as depicted in FIGS. 9-10, inflated balloon 134 contacts and mechanically stimulates muscles 112 along esophagus 108 to cause sequential contractions mimicking the process of deglutition. Once balloon 134 reaches stomach 110, balloon 134 can be deflated through port 126 and dysphagia treatment apparatus 114 can be withdrawn by sliding along nasogastric/enteric tube 120 in the opposite direction. This process can be repeated as desired.

In another embodiment of dysphagia treatment apparatus 114 depicted in FIGS. 12-17, balloon 134 is replaced by one or more radially oriented nozzles 150 fluidly coupled to second lumen 136, with second lumen 136 being fluidly coupled to port 126 as before. Rapid, small-volume, intermittent pulses of air 152 supplied through port 126 can be ejected through nozzles 150 to mechanically stimulate muscles 112 as dysphagia treatment apparatus 114 is advanced through oropharynx 107 and esophagus 108 over nasogastric/enteric tube 120. In a non-limiting embodiment, the air pulses can have a pressure in a ranges of from about 70 millimeters (mm) Hg to about 110 mm Hg, and the air pressure pulse profile can have a Gaussian shape.

Figure 14:
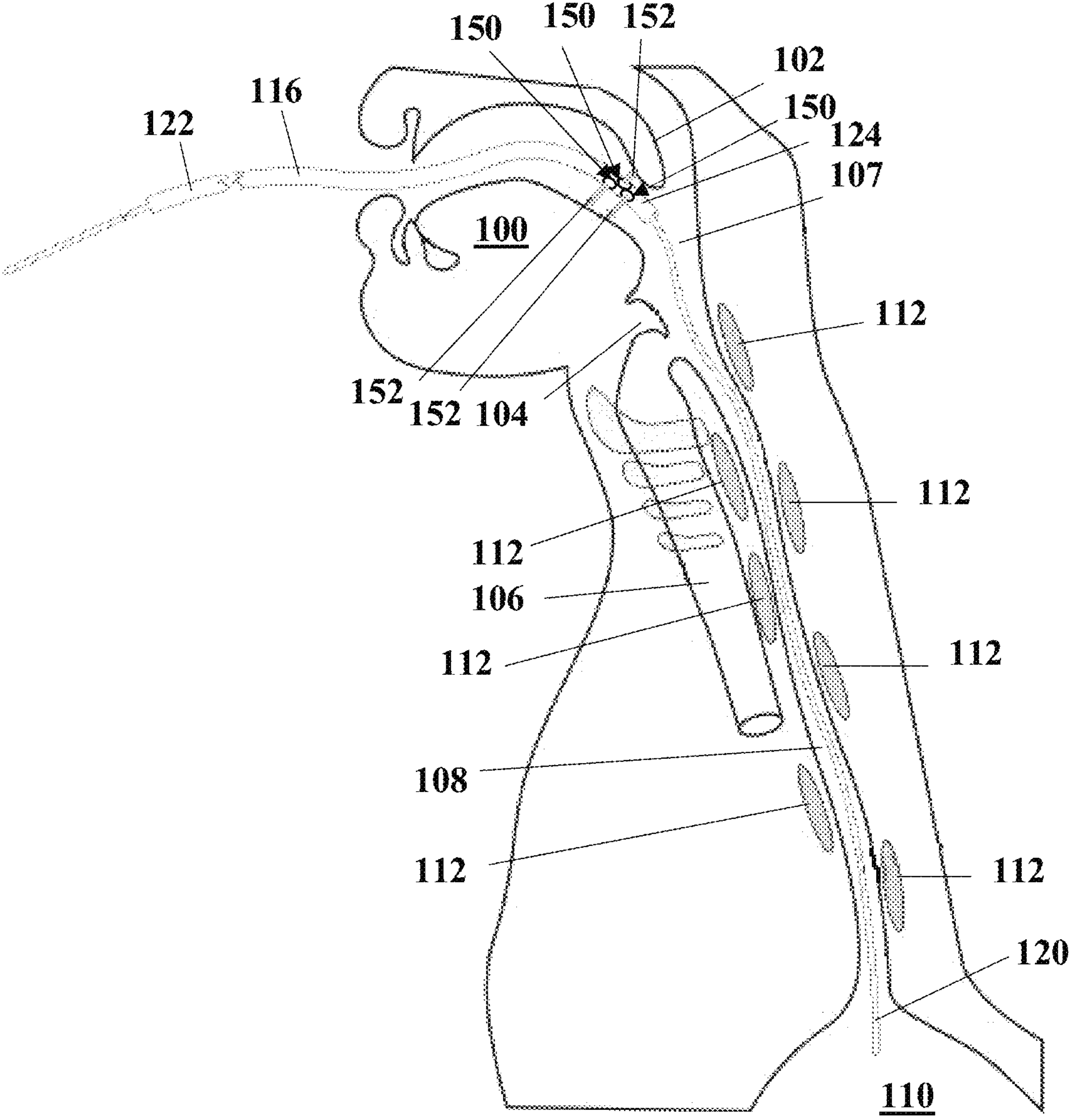
FIG. 14 depicts the apparatus of FIG. 12 in a first stage of advancement into the oropharynx and esophagus over a standard nasogastric tube.
Figure 15:
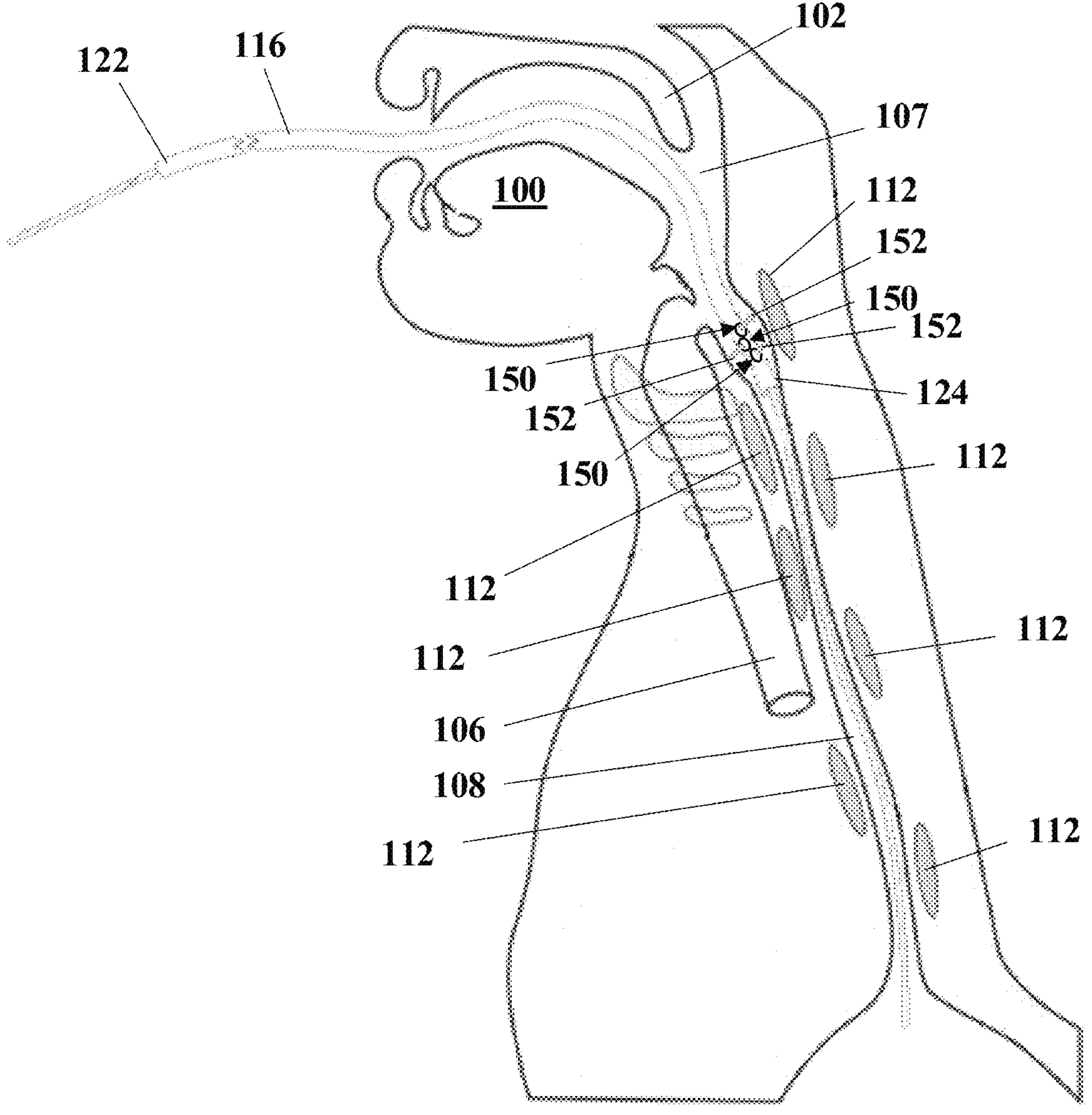
FIG. 15 depicts the apparatus of FIG. 12 in a second stage of advancement into the oropharynx and esophagus over a standard nasogastric tube.
Figure 16:
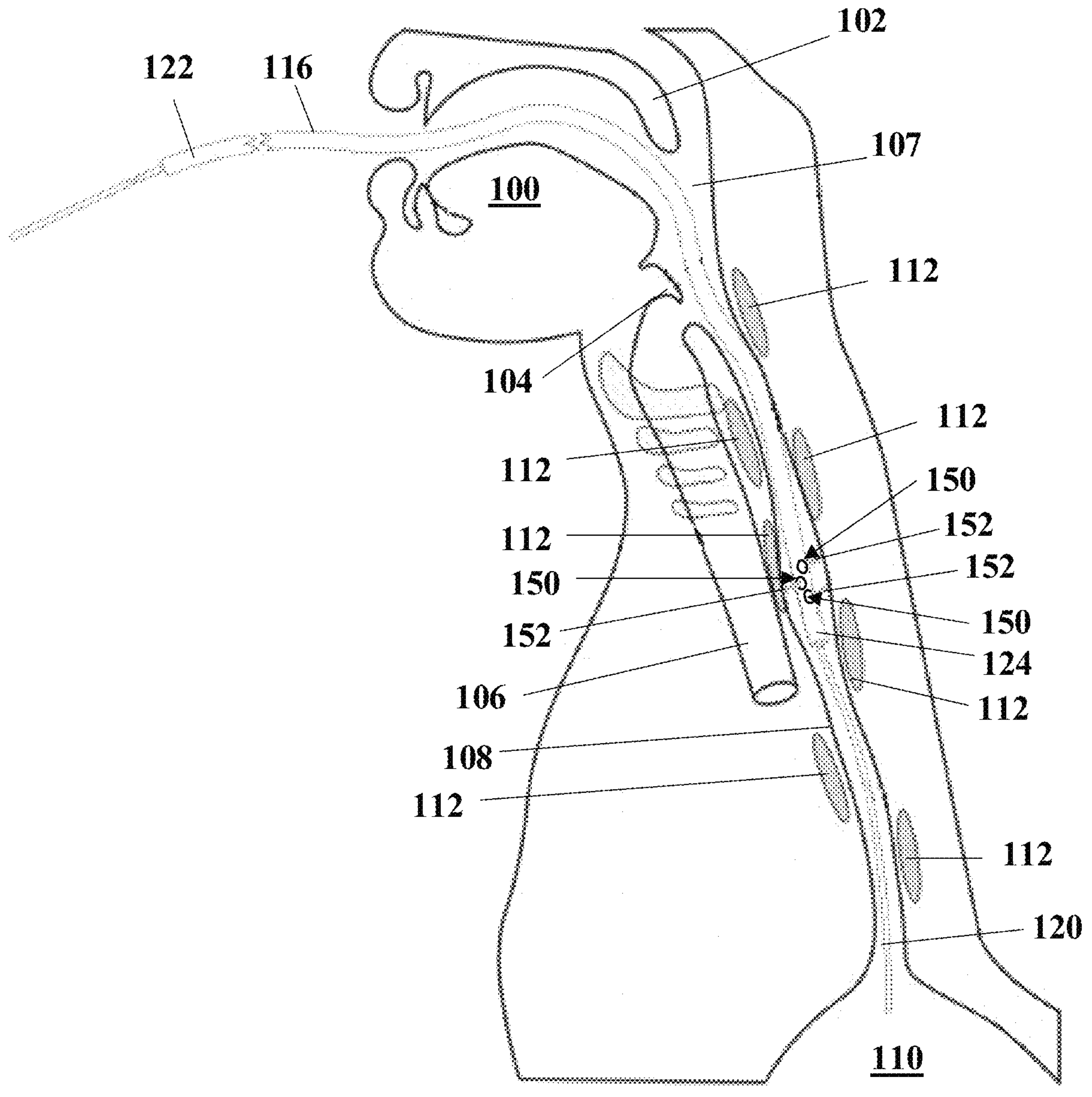
FIG. 16 depicts the apparatus of FIG. 12 in a third stage of advancement into the oropharynx and esophagus over a standard nasogastric tube.
Figures 17, 18, 19:
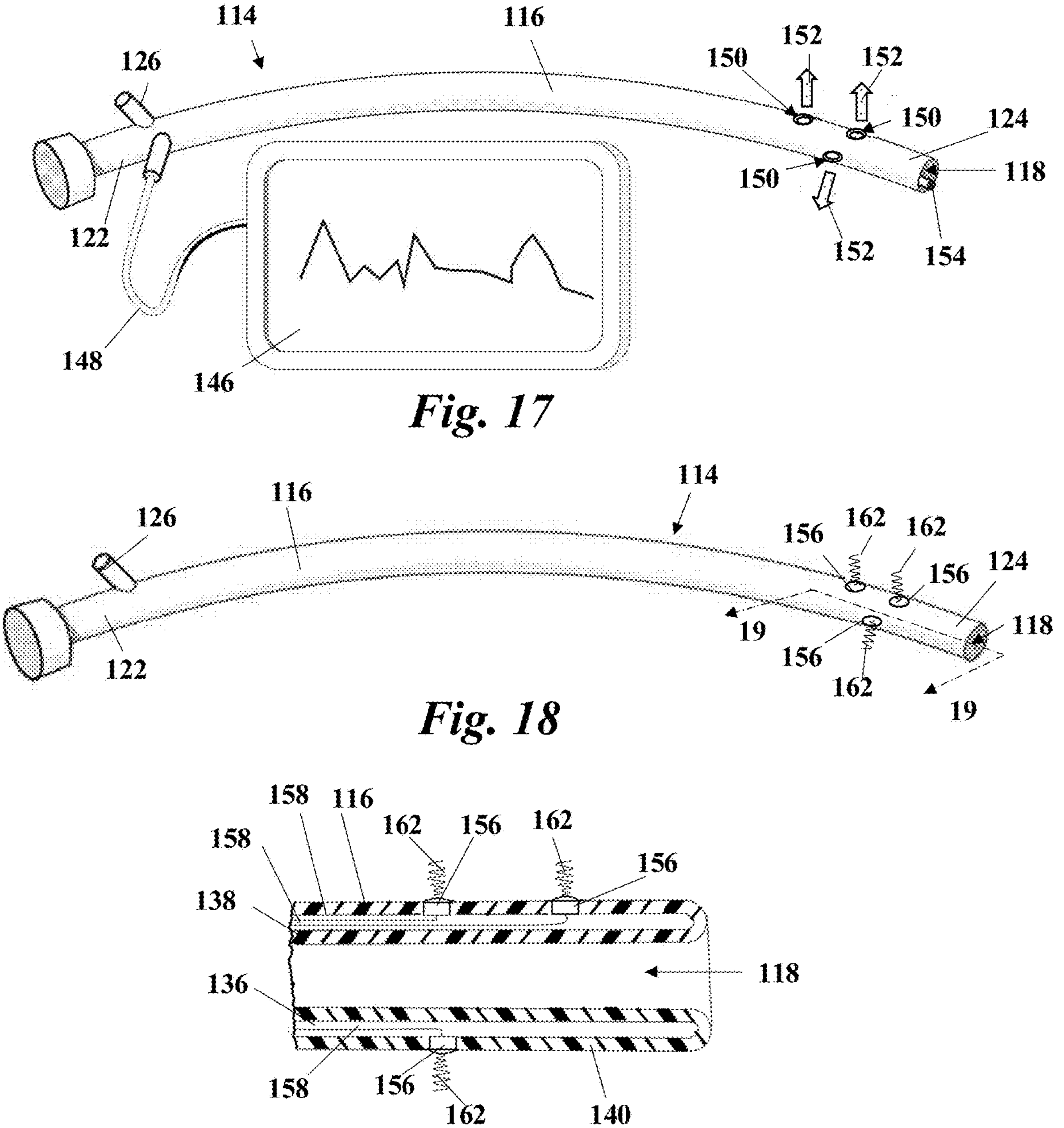
FIG. 17 is an isometric view of the apparatus of FIG. 12, including a display for displaying pressure or velocity of air puffs applied by the apparatus.
FIG. 18 is an isometric view of an apparatus for treating dysphagia according to another embodiment of the invention, in which the apparatus includes light emitters proximate a distal end of the apparatus for applying light to the oropharynx and esophagus.
FIG. 19 is a cross-sectional view of the apparatus of FIG. 18, taken at section 19-19 of FIG. 18.

Once again, in use as depicted in FIGS. 14-16, dysphagia treatment apparatus 114 is advanced into oropharynx 107 and esophagus 108 by introducing proximal end 130 of nasogastric/enteric tube 120 into lumen 118 at distal end 124. As depicted in FIG. 14, once nozzles 150 are in position inside oropharynx 107, air pulses 152 can be applied by injecting air through port 126. As depicted in FIG. 17, one or more pressure transducers 154 can be disposed at distal end 124 and communicatively coupled with external display 146 to enable monitoring and recording of air pressure for measurement and tracking of changes in pressure due to contraction of muscles 112 in oropharynx 107 and esophagus 108 as part of deglutition in response to forward movement of dysphagia treatment apparatus 114. During air pulses 152, the pressure will increase depending upon the contraction of muscles and consequent reduction in space around distal end 124. As dysphagia treatment apparatus 114 is advanced further into esophagus 108 as depicted in FIGS. 15-16, air pulses 152 are applied to the interior of esophagus 108 to mechanically stimulate muscles 112 along esophagus 108 to cause sequential contractions mimicking the process of deglutition. Once distal end 124 reaches stomach 110, dysphagia treatment apparatus 114 can be withdrawn by sliding along nasogastric/enteric tube 120 in the opposite direction. This process can be repeated as desired.

In yet another embodiment of dysphagia treatment apparatus 114 depicted in FIGS. 18-23, one or more light emitters such as light-emitting diodes (LEDs) 156 are provided proximate distal end 124 of dysphagia treatment apparatus 114. LEDs 156 are connected to a suitable power source through leads 158 extending through second lumen 136. It will be appreciated that other light emitting devices could be substituted for LEDs 156. The power source can be contained in controller/display 160, or may be separate. LEDs 156 can be actuated to emit pulses of light 162 to stimulate muscles 112 as dysphagia treatment apparatus 114 is advanced through oropharynx 107 and esophagus 108 over nasogastric/enteric tube 120. In a non-limiting embodiment, the light pulses 162 can be in a range from about 400 nanometers (nm) to about 600 nm wavelength light, predominantly blue, with pulses in a range of from about 10 milliseconds (ms) and 100 ms in duration. It will be appreciated by those skilled in the art, however, that light of other wavelengths and duration could be efficaciously applied while remaining within the scope of the invention.

Figure 20:
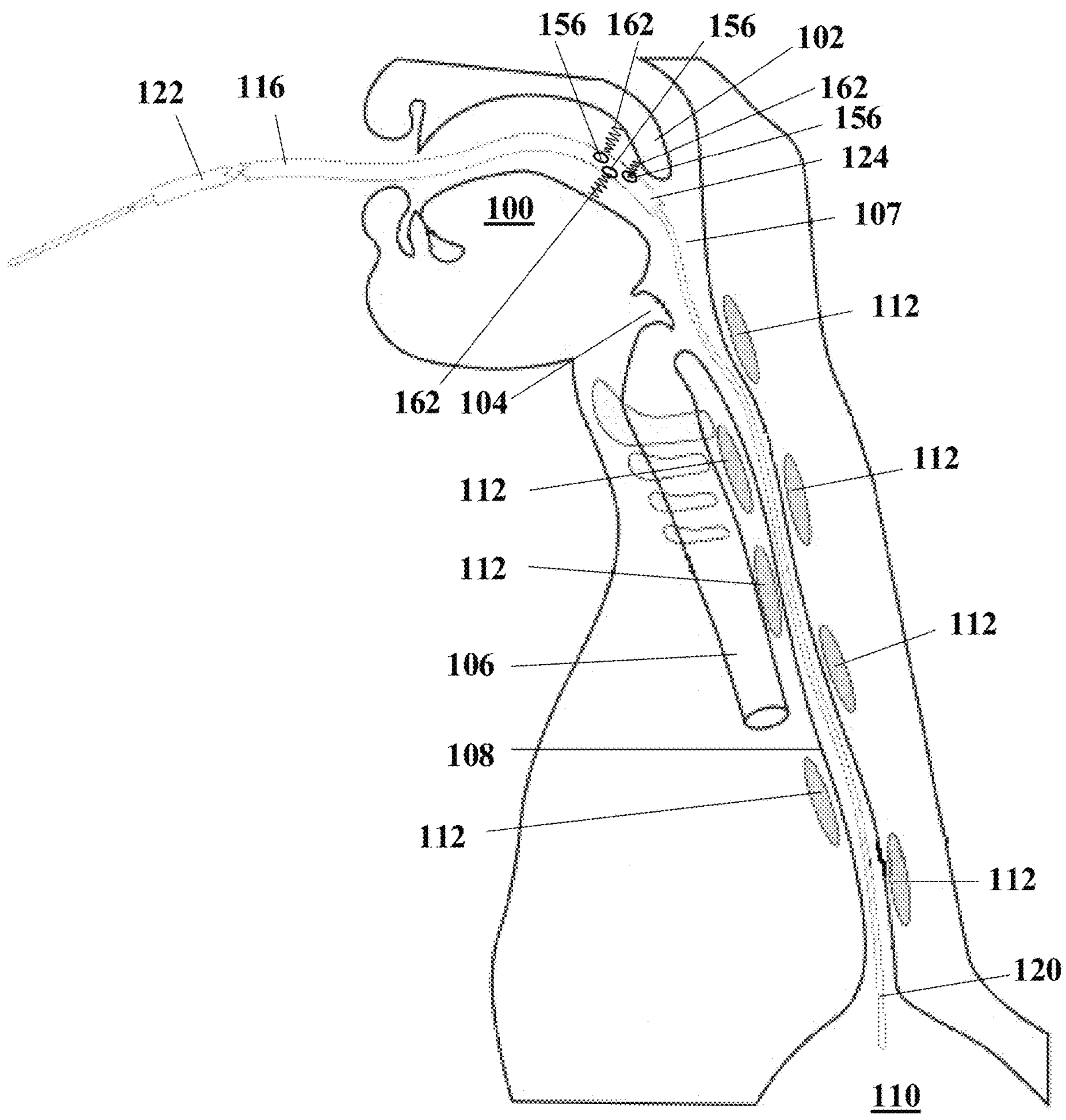
FIG. 20 depicts the apparatus of FIG. 18 in a first stage of advancement into the oropharynx and esophagus over a standard nasogastric tube.
Figure 21:
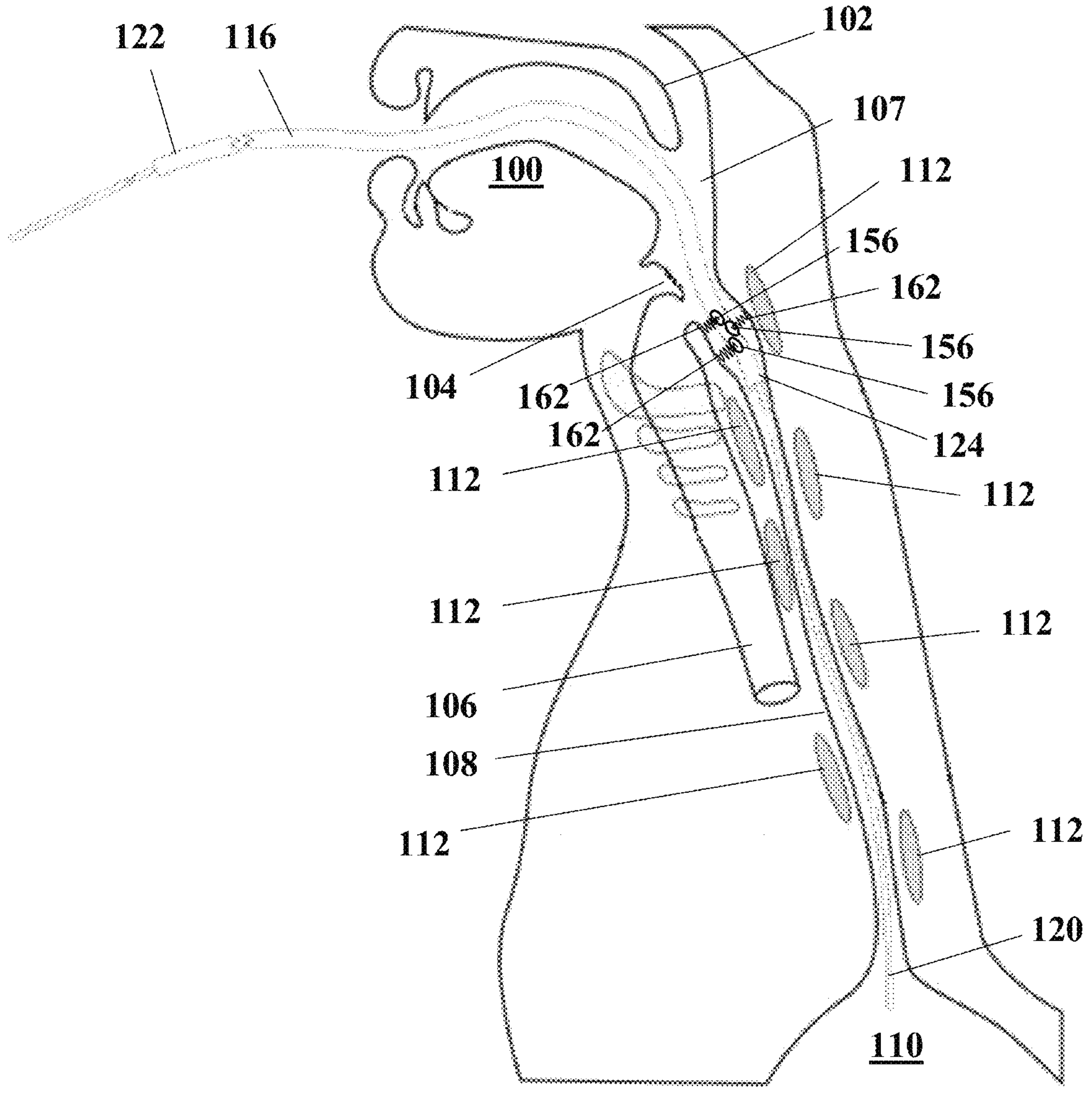
FIG. 21 depicts the apparatus of FIG. 18 in a second stage of advancement into the oropharynx and esophagus over a standard nasogastric tube.
Figure 22:
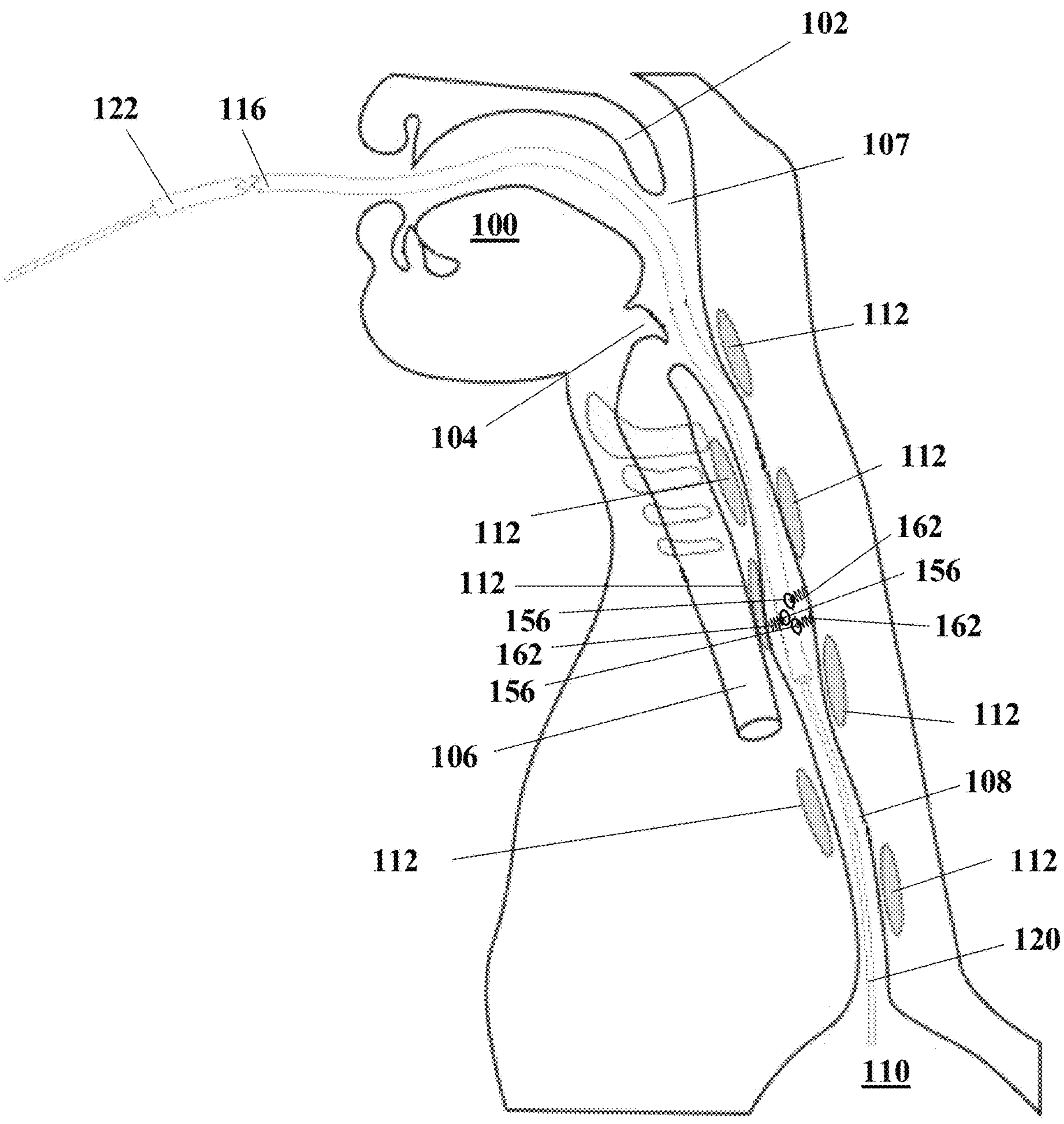
FIG. 22 depicts the apparatus of FIG. 18 in a third stage of advancement into the oropharynx and esophagus over a standard nasogastric tube.

Again, in use as depicted in FIGS. 20-22, dysphagia treatment apparatus 114 is advanced into oropharynx 107 and esophagus 108 by introducing proximal end 130 of nasogastric/enteric tube 120 into lumen 118 at distal end 124. As depicted in FIG. 20, once LEDs 156 are in position inside oropharynx 107, light pulses 162 can be applied by actuating LEDs 156. As dysphagia treatment apparatus 114 is advanced further into esophagus 108 as depicted in FIGS. 21-22, light pulses 162 are applied to the interior of esophagus 108 to stimulate muscles 112 along esophagus 108 to cause sequential contractions mimicking the process of deglutition. Once distal end 124 reaches stomach 110, dysphagia treatment apparatus 114 can be withdrawn by sliding along nasogastric/enteric tube 120 in the opposite direction. This process can be repeated as desired.

Figure 23:
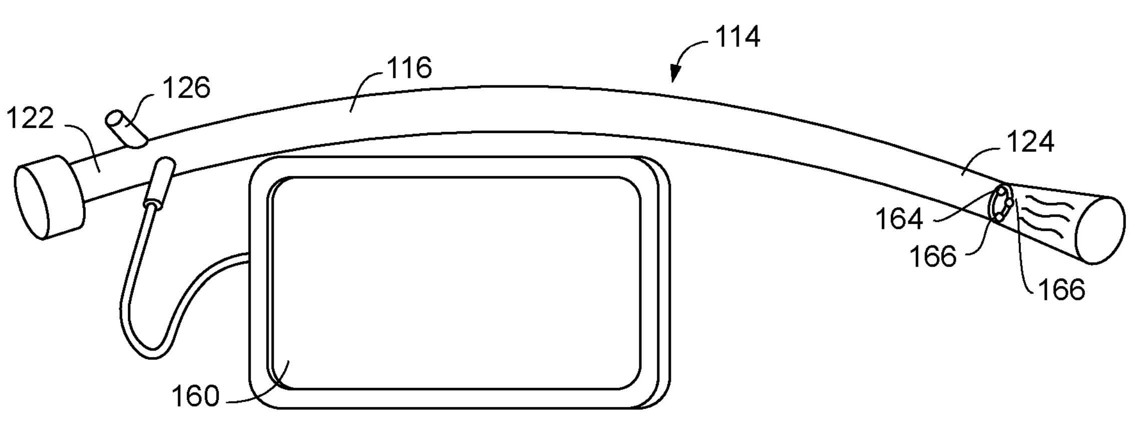
FIG. 23 is an isometric view of an apparatus for treating dysphagia according to an embodiment of the invention, in which the apparatus includes a camera at the distal end of the apparatus and a display for displaying images from the camera.

Moreover, as depicted in FIG. 23, high-resolution camera 164 with lighting 166 can be disposed at distal end 124 and communicatively coupled with controller/display 160 to enable visualization on controller/display 160 of contraction of muscles 112 in oropharynx 107 and esophagus 108 as part of deglutition in response to forward movement of dysphagia treatment apparatus 114.

Depicted in FIGS. 24-35 are further embodiments of a dysphagia treatment apparatus 168. Apparatus 168 generally includes sleeve 170 disposed on, and affixed to, outer surface 172 of nasogastric/enteric tube 120. Sleeve 170 is flexible, resilient, and expandable and can be formed as a thin layer of bioplastic polymer such as polyethylene or polylactic acid, although other polymer materials capable of being formed into a thin expandable structure could also be used while remaining within the scope of the invention. Sleeve 170 will typically be from about to about 70 mm in length and positioned along standard nasogastric/enteric tube 120 so as to correspond to oropharynx 107 and esophagus 108 when nasogastric/enteric tube 120 is emplaced in a patient. Sleeve 170 is sealed to outer surface 172 of nasogastric/enteric tube 120 at proximal end 174 and distal end 176. An air/saline bolus injected into sleeve 170 at proximal end 174 can move down sleeve 170 propelled toward stomach 110 by sequential contraction of oropharyngeal and esophageal muscles 112.

In embodiments of the invention as depicted in FIGS. 26-32, sleeve 170 is divided into segments forming a plurality of expandable chambers 178 longitudinally along nasogastric/enteric tube 120. In the embodiment depicted in FIGS. 26 and 27, dividers in the form of non-compliant rings 180 made from polymer material are provided at intervals along sleeve 170. In a preferred embodiment, rings 180 will have a longitudinal dimension X of from about 3 cm to about 5 cm and will be spaced-apart by a longitudinal dimension Y of from about 3 cm to about 7 cm. Rings 180 can be secured to outer surface 181 of sleeve 170 with adhesive. Injection port 183 is provided to enable injection of air, liquid such as saline, or a combination thereof to the proximal-most chamber 185 of chambers 178.

In the embodiment depicted in FIGS. 28-30, sleeve 170 is partially adhered to outer surface 172 of nasogastric/enteric tube 120 at adhesion regions 182 to form dividers, for example by fusing the plastic materials of sleeve 170 and nasogastric/enteric tube 120 or with separate adhesive. Again, adhesion regions can be spaced-apart along sleeve 170 by a longitudinal distance Y of from about 3 cm to about 7 cm. Injection port 183 is provided to enable injection of air, liquid such as saline, or a combination thereof to the proximal-most chamber 185 of chambers 178.

Figure 31:
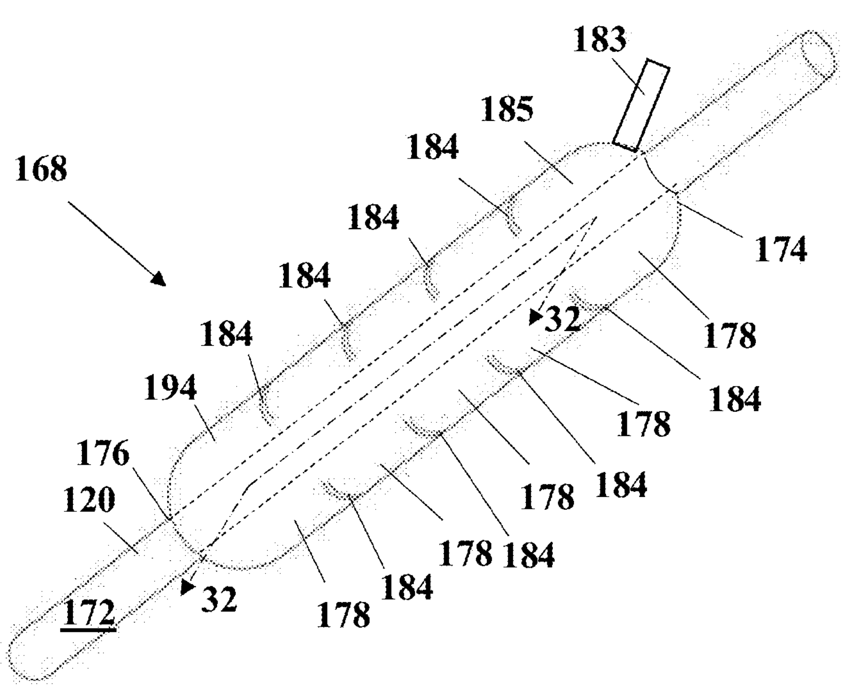
FIG. 31 is an isometric view of a sleeve receivable over a standard nasogastric tube in which septa are defined between the outer portion of the sleeve and the central lumen.
Figure 32:
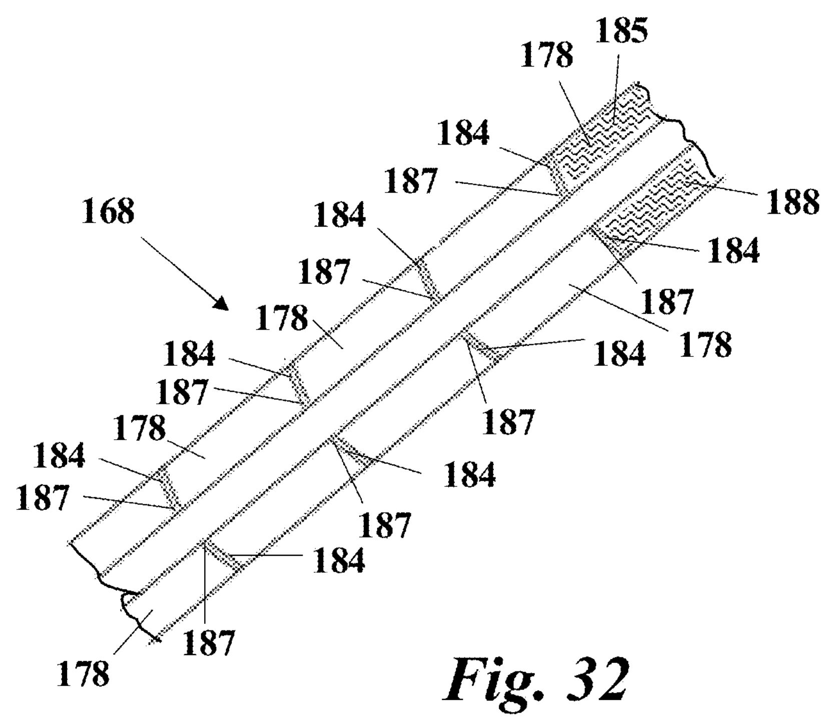
FIG. 32 is a cross-sectional view of device of FIG. 31 taken at section 32-32 of FIG. 31.

In the embodiment of FIGS. 31 and 32, flexible partial septa 184 project inwardly from sleeve 170 toward outer surface 172 of nasogastric/enteric tube 120. Free-end 187 of each septum 184 is free to deflect to enable the passage of air/liquid bolus 188. As depicted in FIG. 32, septa 184 can be angled slightly toward distal end 176. Injection port 183 is provided to enable injection of air, liquid such as saline, or a combination thereof to the proximal-most chamber 185 of chambers 178.

Figure 24:
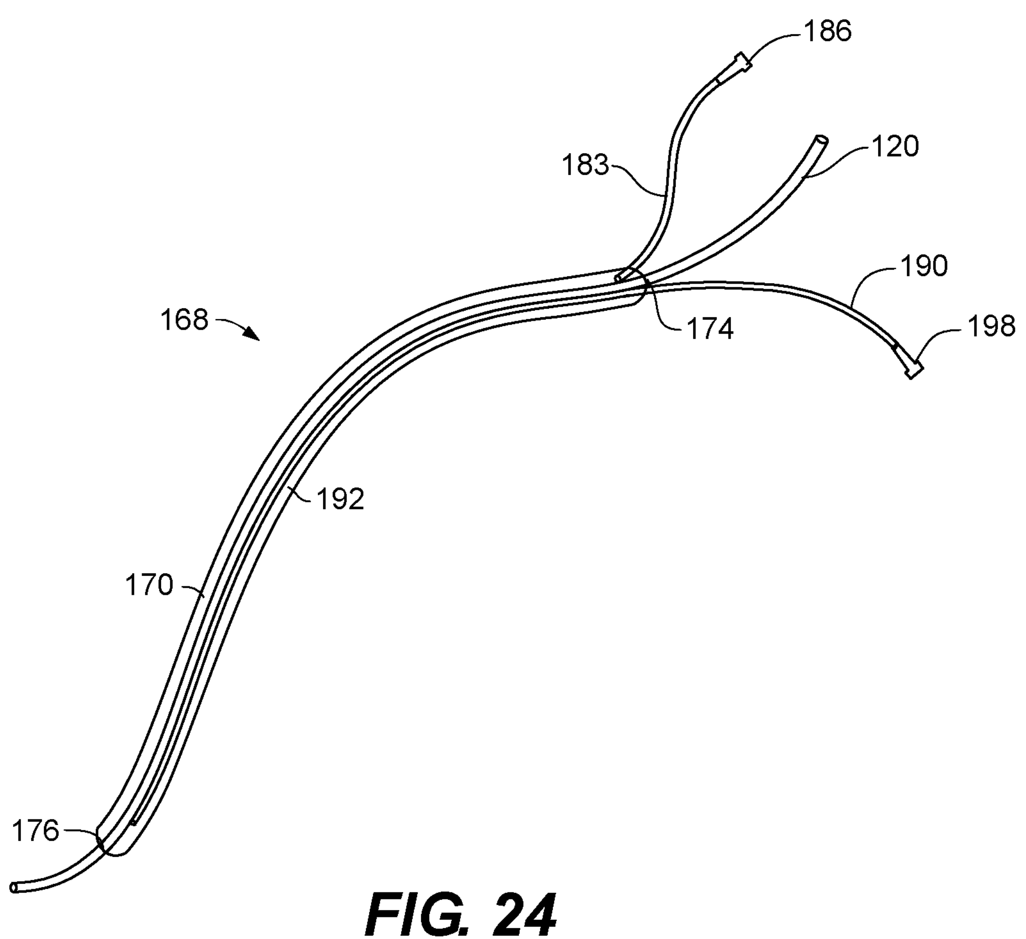
FIG. 24 is an isometric view of an apparatus for treating dysphagia according to an embodiment of the invention, in which the apparatus includes a sleeve received over a standard nasogastric tube.
Figure 25:
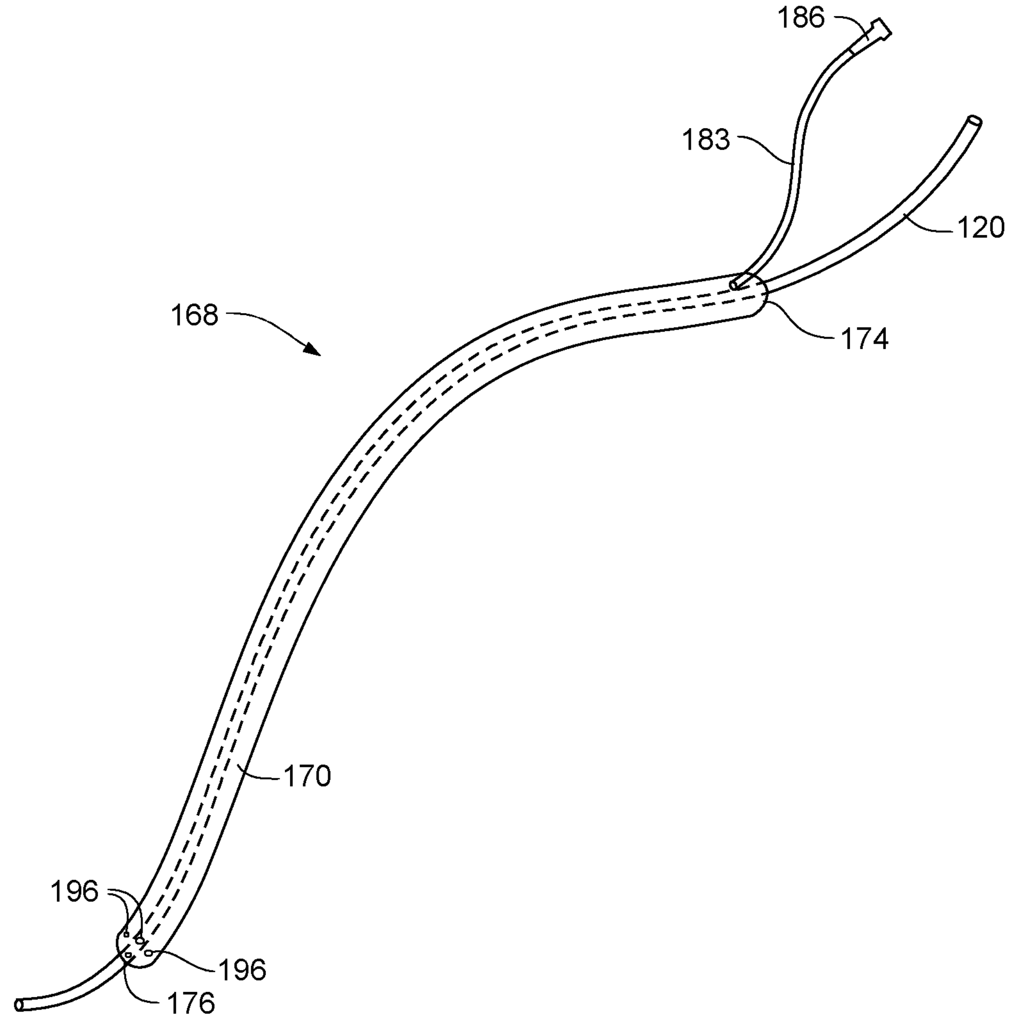
FIG. 25 is an isometric view of another apparatus for treating dysphagia according to an embodiment of the invention, in which the apparatus includes a sleeve received over a standard nasogastric tube.
Figures 26, 27:
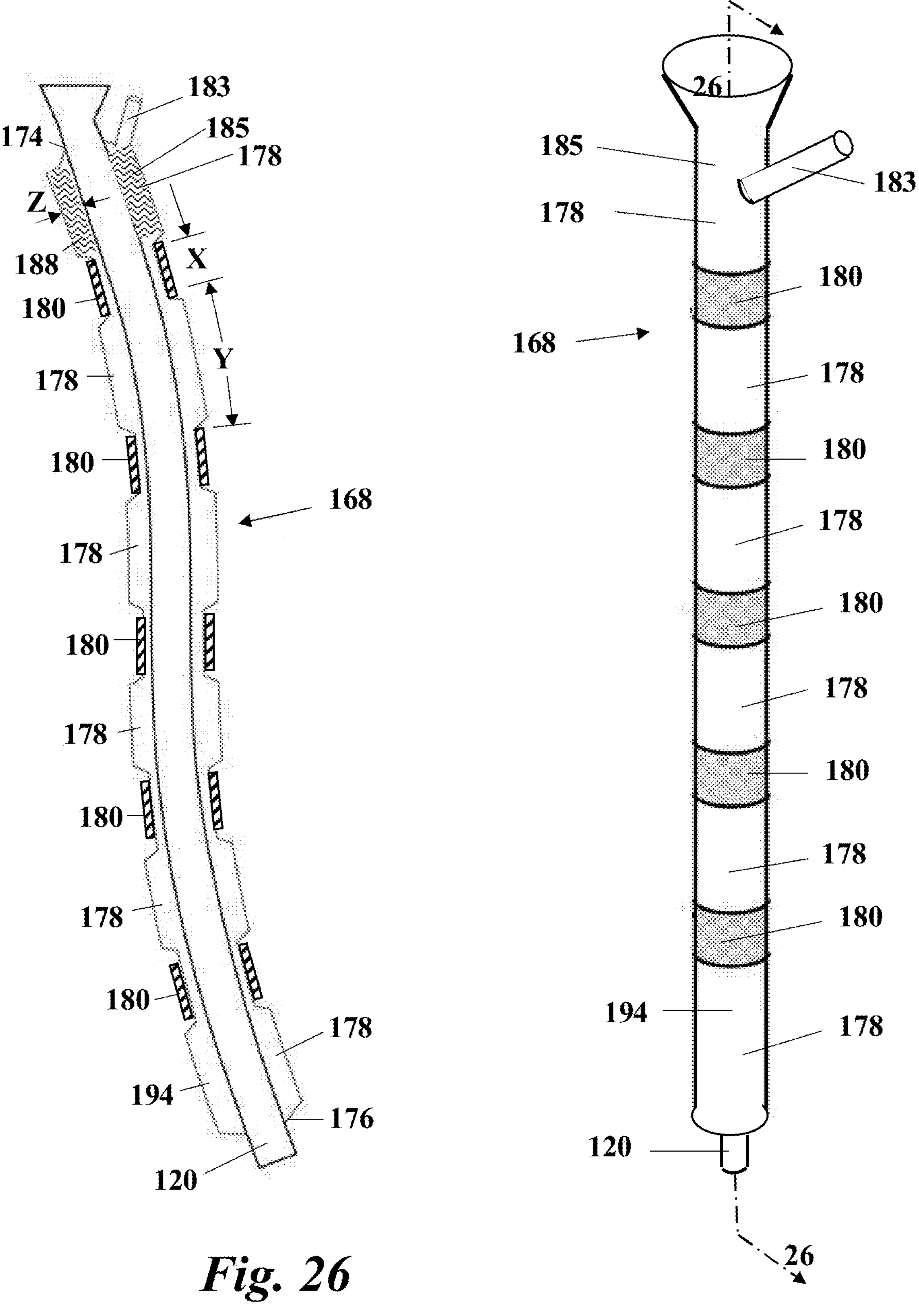
FIG. 26 is a cross-sectional view, taken at section 26-26 of FIG. 27, of another apparatus for treating dysphagia according to an embodiment of the invention, in which the apparatus includes a sleeve received over a standard nasogastric tube.
FIG. 27 is an isometric view of the apparatus of FIG. 26.

As depicted in FIG. 24, port 183 can have proximal end 186 adapted to receive a syringe (not depicted), enabling injection of the air, liquid, or air/liquid bolus 188 into proximal-most chamber 185. Aspiration port 190 can be provided, connected with a small tube 192 extending through sleeve 170 to distal-most chamber 194 to enable extraction of air/liquid bolus 188 once it reaches distal end 176 of sleeve 170. Proximal end 198 of aspiration port 190 can be adapted to receive a syringe (not depicted) to enable extraction of the bolus 188. Alternatively, as depicted in FIG. 25, distal end 176 of sleeve 170 can be provided with holes 196 to enable air/liquid bolus 188 to empty into stomach 110.

In any of the forgoing embodiments of dysphagia treatment apparatus 168, pressure transducers (not depicted) can be provided in sleeve 170 to enable monitoring and recording of pressure inside sleeve 170 to evaluate the contraction of muscles 112 in oropharynx 107 and esophagus 108 as part of deglutition.

Figure 33:
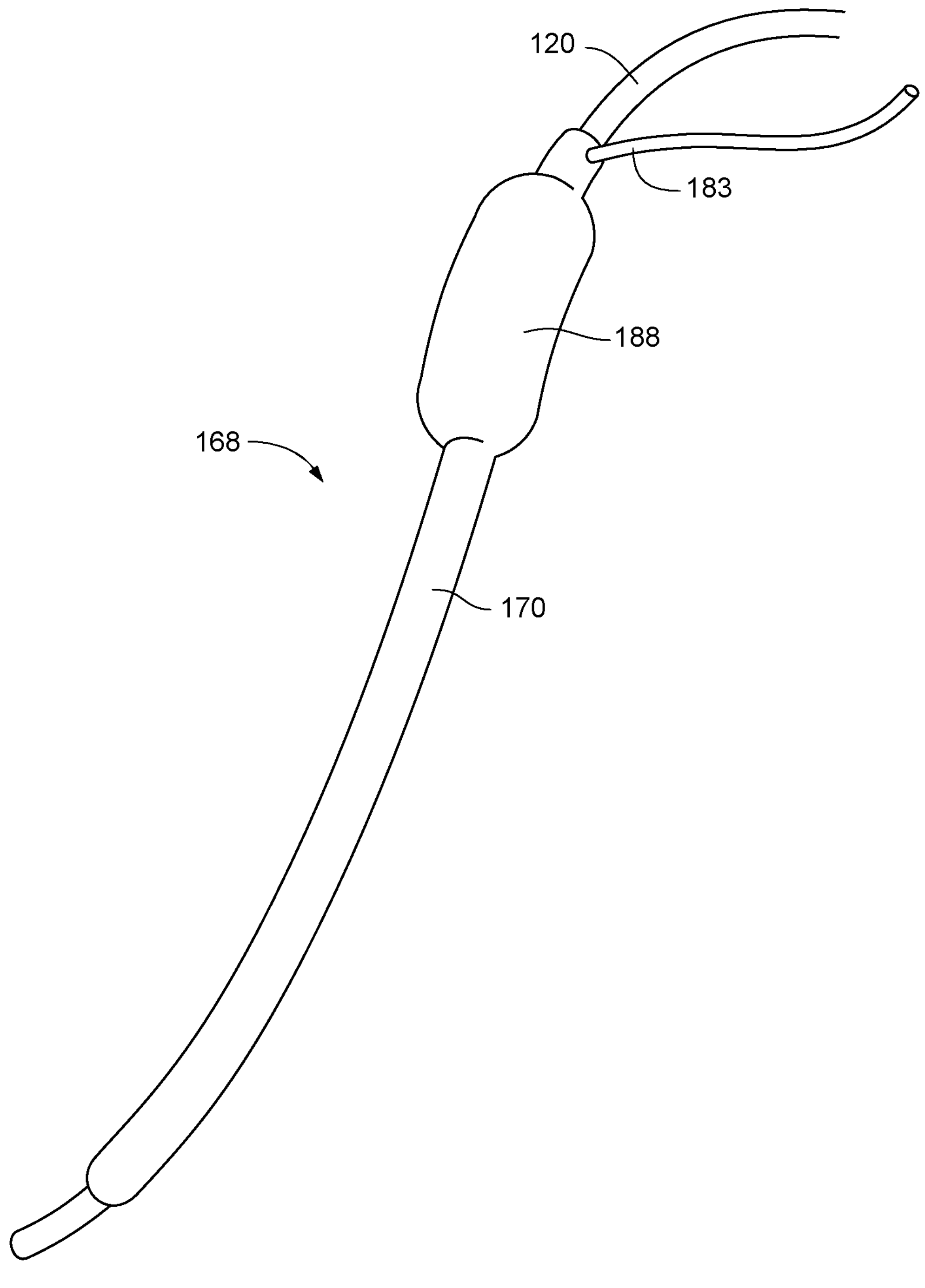
FIG. 33 is an isometric view of the sleeves of FIGS. 24-32 in which an air/saline bolus has been introduced into the sleeve.
Figure 34:
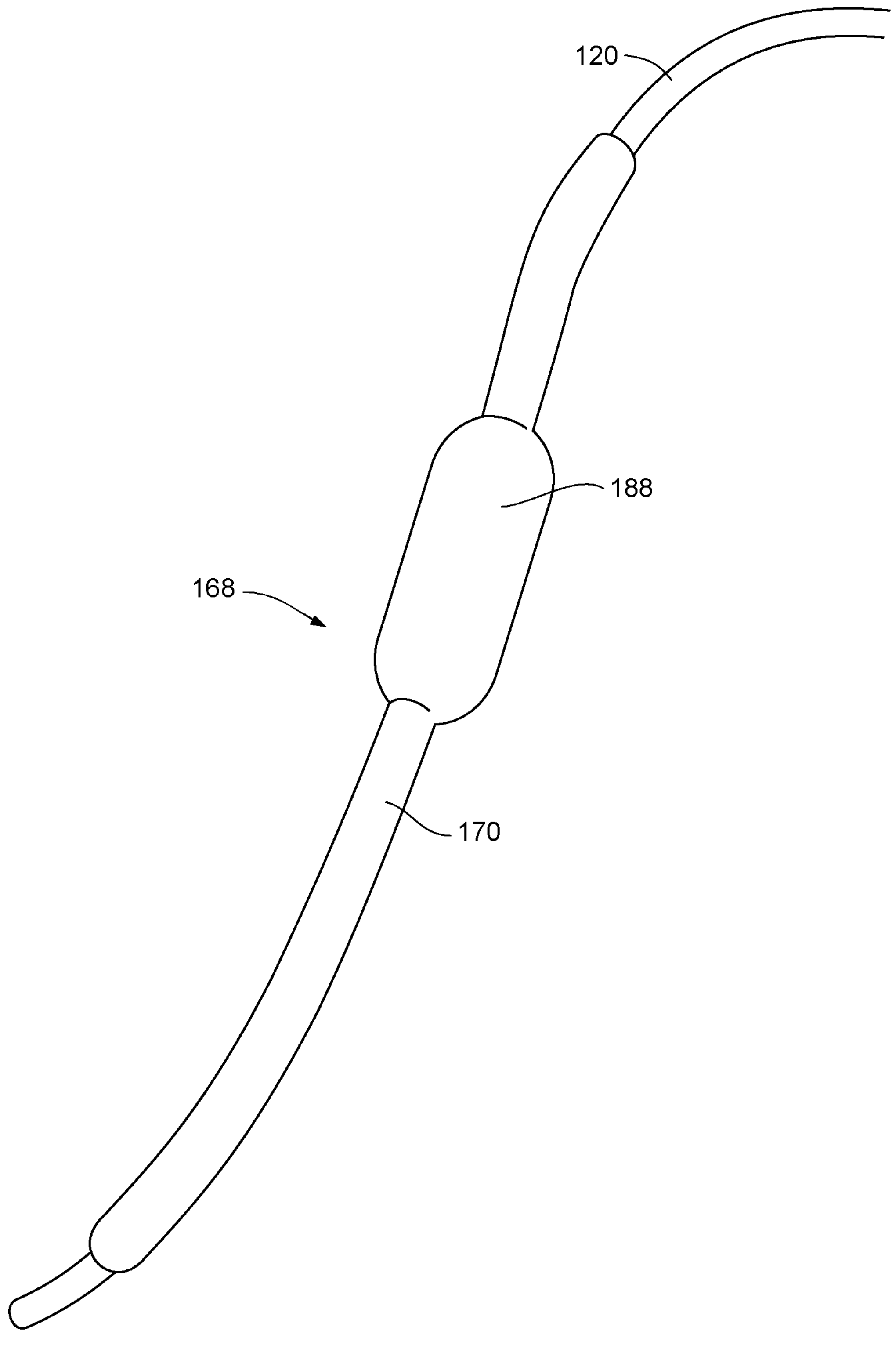
FIG. 34 is an isometric view of the device of FIG. 33 in which the air/saline bolus has moved further along the sleeve due to esophageal muscle contraction.
Figure 35:
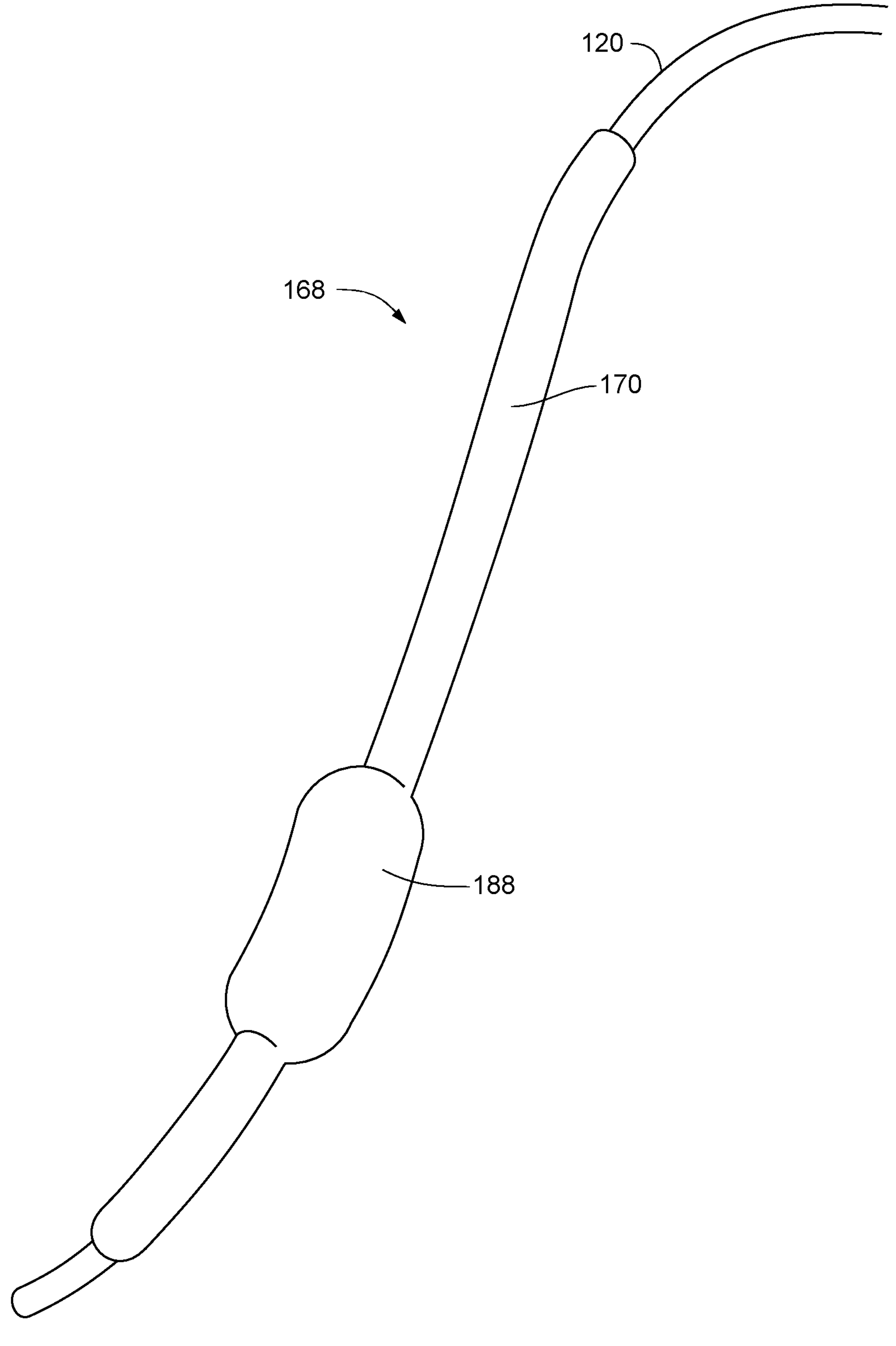
FIG. 35 is an isometric view of the apparatus of FIG. 33, in which the air/saline bolus has moved still further along the sleeve due to esophageal muscle contraction.

In use, with nasogastric/enteric tube 120 and sleeve 170 emplaced in the oropharynx 107 and esophagus 108, bolus 188 is injected into proximal-most chamber 185 through port 183. Preferably, a sufficient amount of air/liquid is injected so that bolus 188 expands chamber 185 by a lateral dimension Z of from about 2 mm to about 5 mm. As depicted in FIGS. 33-35, bolus 188 is propelled from proximal end 174 to distal end 176 through successive chambers 178 through contraction of muscles 112 in oropharynx 107 and esophagus 108. Rings 180, adhesion regions 182, or septa 184 inhibit reflux of bolus 188 toward proximal end 174. Once bolus 188 reaches distal end 176, bolus 188 can be evacuated through aspiration port 190 or drained into stomach 110 through holes 196.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc., have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An apparatus for treating dysphagia, comprising:

an elongate tubular body presenting a proximal end, a distal end, and defining a first lumen and a second lumen, the first lumen oriented along a longitudinal axis of the tubular body, the first lumen adapted to receive a nasogastric/enteric tube therein such that the elongate tubular body is selectively slidably shiftable relative to the nasogastric/enteric tube, the second lumen being oriented parallel to the first lumen; and a dysphagia treatment device disposed proximate the distal end of the elongate tubular body, wherein the dysphagia treatment device is selectively shiftable with the elongate tubular body between a first position proximate a proximal end of the nasogastric/enteric tube and a second position proximate a distal end of the nasogastric/enteric tube, and wherein the dysphagia treatment device is selectively actuatable as the elongate tubular body slides over the nasogastric/enteric tube.

2. The apparatus of claim 1, wherein the dysphagia treatment device comprises an inflatable balloon, the balloon being selectively inflatable with fluid supplied through the second lumen.

3. The apparatus of claim 2, further comprising at least one pressure transducer for measuring fluid pressure in the balloon.

4. The apparatus of claim 3, wherein the at least one pressure transducer is communicatively coupled to an external display.

5. The apparatus of claim 1, wherein the tubular body includes a port disposed proximate the proximal end of the tubular body and fluidly coupled to the second lumen for supplying and removing fluid from the second lumen and the balloon.

6. The apparatus of claim 1, wherein the dysphagia treatment device comprises at least one air nozzle extending from the second lumen to an exterior surface of the tubular body, the at least one air nozzle oriented transverse to the longitudinal axis of the tubular body.

7. The apparatus of claim 6, further comprising at least one pressure transducer disposed at the distal end of the elongate tubular body.

8. The apparatus of claim 7, wherein the at least one pressure transducer is communicatively coupled to an external display.

9. The apparatus of claim 6, wherein the tubular body includes a port disposed proximate the proximal end of the tubular body and fluidly coupled to the second lumen for supplying air to the second lumen and the at least one air nozzle.

10. The apparatus of claim 1, wherein the dysphagia treatment device comprises at least one light emitter arranged to emit light in a direction transverse to the longitudinal axis of the tubular body.

11. The apparatus of claim 10, wherein the at least one light emitter emits light pulses having a wavelength in a range of from about 400 nm to about 600 nm and a duration in a range of from about 10 ms to about 100 ms.

12. The apparatus of claim 10, wherein the at least one light emitter is an LED.

13. The apparatus of claim 10, further comprising at least one pressure transducer disposed at the distal end of the elongate tubular body.

14. The apparatus of claim 13, wherein the at least one pressure transducer is communicatively coupled to an external display.

15. The apparatus of claim 10, further comprising a high-resolution camera disposed at the distal end of the tubular body, the camera communicatively coupled to a video display.

16. A method for treating dysphagia, comprising:

providing a dysphagia treatment apparatus comprising:

an elongate tubular body presenting a proximal end, a distal end, and defining a first lumen and a second lumen, the first lumen oriented along a longitudinal axis of the tubular body, the first lumen adapted to receive a nasogastric/enteric tube therein such that the elongate tubular body is selectively slidably shiftable relative to the nasogastric/enteric tube, the second lumen being oriented parallel to the first lumen; and a dysphagia treatment device disposed proximate the distal end of the elongate tubular body;

introducing a proximal end of a nasogastric/enteric tube emplaced in the nasopharynx and esophagus of a patient into the first lumen at the distal end of the elongate tubular body;

sliding the elongate tubular body over the nasogastric/enteric tube to advance the elongate tubular body into the nasopharynx and esophagus of the patient while periodically actuating the dysphagia treatment device to stimulate muscles controlling deglutition in the nasopharynx and esophagus of the patient.

17. The method of claim 16, wherein the dysphagia treatment device comprises an inflatable balloon, and the step of actuating the dysphagia treatment device comprises inflating the balloon with fluid.

18. The method of claim 16, wherein the dysphagia treatment device comprises at least one air nozzle, and the step of actuating the dysphagia treatment device comprises applying pulses of air to the nasopharynx and esophagus of the patient with the at least one air nozzle.

19. The method of claim 18, wherein the air pulses have a pressure in a range of about 70 mm Hg to about 110 mm Hg.

20. The method of claim 16, wherein the dysphagia treatment device comprises at least one light emitter, and the step of actuating the dysphagia treatment device comprises applying pulses of light to the nasopharynx and esophagus of the patient with the at least one light emitter.

21. The method of claim 20, wherein the light pulses have a wavelength in a range of from about 400 nm to about 600 nm and a duration in a range of from about 10 ms to about 100 ms.

22. The apparatus of claim 6, wherein the at least one air nozzle is adapted to emit air pulses having a pressure in a range of about 70 mm Hg to about 110 mm Hg.

* * * * *